(12) United States Patent
Leyssens et al.

(10) Patent No.: US 11,535,604 B2
(45) Date of Patent: Dec. 27, 2022

(54) FASORACETAM CRYSTALLINE FORMS

(71) Applicant: The Children's Hospital of Philadelphia, Philadelphia, PA (US)

(72) Inventors: Tom Leyssens, Jette (BE); Bram Harmsen, GroB-Zimmern (DE)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 16/963,494

(22) PCT Filed: Jan. 17, 2019

(86) PCT No.: PCT/US2019/014027
§ 371 (c)(1),
(2) Date: Jul. 20, 2020

(87) PCT Pub. No.: WO2019/143829
PCT Pub. Date: Jul. 25, 2019

(65) Prior Publication Data
US 2021/0047288 A1 Feb. 18, 2021

Related U.S. Application Data

(60) Provisional application No. 62/619,031, filed on Jan. 18, 2018, provisional application No. 62/668,108, filed on May 7, 2018, provisional application No. 62/683,419, filed on Jun. 11, 2018.

(51) Int. Cl.
*C07D 401/06* (2006.01)
(52) U.S. Cl.
CPC ........ *C07D 401/06* (2013.01); *C07B 2200/13* (2013.01)
(58) Field of Classification Search
CPC .......................... C07D 401/06; C07B 2200/13
USPC ........................................................ 546/208
See application file for complete search history.

(56) References Cited

U.S. PATENT DOCUMENTS

| 5,102,882 A | 4/1992 | Kimura et al. |
| 2017/0083664 A1 | 3/2017 | Hakonarson et al. |

FOREIGN PATENT DOCUMENTS

| WO | 2017/044491 A1 | 3/2017 |
| WO | 2017/044497 A1 | 3/2017 |
| WO | 2017/044502 A1 | 3/2017 |
| WO | 2017/044503 A1 | 3/2017 |
| WO | 2018/048868 A1 | 3/2018 |

OTHER PUBLICATIONS

International Search Report, dated Apr. 8, 2019, for International Application No. PCT/US2019/014027, filed Jan. 17, 2019.
Harmsen et al., "A Study of Fasoracetam's Solid State Forms: A Potential Anti-Alzheimer Pharmaceutical," Journal of Pharmaceutical Sciences, vol. 106, No. 5, 2017, pp. 1-5.
Extended European Search Report, dated Sep. 15, 2021, issued in corresponding European Patent Application No. 19740868.5.
Search Report and Written Opinion, dated May 14, 2021, issued in corresponding Singapore Patent Application No. 11202006813T.
Hirouchi et al., "Role of metabotropic glutamate receptor subclasses in modulation of adenylyl cyclase activity by a nootropic NS-105," European Journal of Pharmacology, vol. 387, No. 1, Nov. 3, 2000, pp. 9-17.
Lee et al., "Pharmaceutical Analysis," Blackwell Publishing Ltd., 2003, pp. 225-257.

*Primary Examiner* — Charanjit Aulakh
(74) *Attorney, Agent, or Firm* — Kathleen D. Rigaut; Howson & Howson LLP

(57) ABSTRACT

The disclosure is directed to crystalline forms and mixtures thereof of R-fasoracetam. Such crystalline forms include Form II monohydrate R-fasoracetam and the anhydrate form of R-fasoracetam. The disclosure further includes mixtures of the anhydrate form of R-fasoracetam together with one or more of Form I monohydrate R-fasoracetam and Form II monohydrate R-fasoracetam.

3 Claims, 25 Drawing Sheets

ORTEP of R-fasoracetam anhydrate

ORTEP of R-fasoracetam monohydrate Form I

FASORACETAM CRYSTALLINE FORMS

This application is a § 371 of International Application No. PCT/US2019/014027, filed Jan. 17, 2019, which claims the benefit of priority to United States Provisional Application No. 62/619,031, filed Jan. 18, 2018; United States Provisional Application No. 62/668,108, filed May 7, 2018; and United States Provisional Application No. 62/683,419, filed Jun. 11, 2018; all of which are incorporated by reference in their entirety.

Recently, a precision-medicine-based clinical trial was completed reporting successful treatment of attention deficit hyperactive disorder (ADHD) in subjects having at least one genetic alteration in a metabotropic glutamate receptor (mGluR) network gene. In that study, subjects having a genetic alteration in an mGluR network gene were successfully treated with fasoracetam (NFC-1), which has been shown in vitro to be a nonselective activator against all classes of mGluRs (See Hirouchi M, et al. (2000) European Journal of Pharmacology 387:9-17; see also WO2017/044491). Fasoracetam has also been successful in treating subjects having ADHD and 22q11.2 Deletion Syndrome (see, e.g., WO2017/044491), anxiety (see, e.g., WO2017/044503), conduct disorder (see, e.g., WO2017/044502), Tourette's syndrome (see, e.g., WO2017/044497), and suggested for treatment of anorexia (see, e.g., PCT/US2017/050228). Fasoracetam is orally available and to date has typically been made available as a monohydrate. Fasoracetam has one chiral center and the R-enantiomer has been developed clinically in the form of R-fasoracetam monohydrate Form I. We identified a stable hydrate form (hydrate I), and also a second polymorphic form of the hydrate (hydrate II). Using specific conditions, an anhydrate form could also be isolated.

All references disclosed herein are incorporated by reference in their entirety.

Disclosed herein are solid forms of fasoracetam. Various spectroscopic and crystallographic techniques may be used to characterize solid forms of compounds such as, for example, a polymorph, a hydrate, a polymorph of a hydrate, or an anhydrate. These include XRPD, single-crystal x-ray, Raman spectroscopy, infrared spectroscopy, and solid-state NMR spectroscopy, among other techniques. Different solid forms of the same compound often also exhibit distinct thermal behavior. Thermal behavior may be analyzed by such techniques as capillary melting point, thermogravimetric analysis (TGA), and differential scanning calorimetry (DSC) to name a few. These techniques can be used to identify and characterize such solid forms.

The data from a technique may be used in multiple ways to characterize a solid form. For example, the entire XRPD pattern output from a diffractometer may be used to characterize such a solid form such as, for example, a polymorph, a hydrate, a polymorph of a hydrate, or an anhydrate. A compound is polymorphic if there are two or more crystalline structures of that compound with each crystalline structure being a polymorph of the compound. A smaller subset of such data, however, may also be, and typically is, suitable for such characterization. For example, a collection of one or more peaks from such a pattern may be so used. Indeed, often even a single XRPD peak may be used for such characterization. When a solid form herein, or a mixture of solid forms herein, is characterized by "one or more peaks" of an XRPD pattern and such peaks are listed, what is meant is that any combination of the peaks listed may be used to characterize the solid form such as, for example, a polymorph, a hydrate, a polymorph of a hydrate, or an anhydrate, or mixture thereof. Further, the fact that other peaks are present in the XRPD pattern, does not negate or otherwise limit the characterization.

Similarly, subsets of spectra of other techniques may be used alone or in combination with other analytical data for characterization purposes. DSC measurements may also be used for such characterization purposes.

An XRPD pattern is an x-y graph with °2Θ (diffraction angle) on the x-axis and intensity on the y-axis. The pattern contains peaks which may be used to characterize solid forms. The peaks are usually represented and referred to by their position on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the pharmaceutical arts to characterize solid forms.

As with any data measurement, there is variability in x-ray powder diffraction. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline material. Likewise, different software packages process x-ray data differently and this also leads to variability. These and other sources of variability are known to those of ordinary skill in the pharmaceutical arts.

Due to such sources of variability, it is common to recite x-ray diffraction peaks using the word "about" prior to the peak value in °2Θ which presents the data to within 0.1 or 0.2 °2Θ of the stated peak value depending on the circumstances. All x-ray powder diffraction peaks cited herein are reported with a variability on the order of 0.2 degree °2Θ and are intended to be reported with such a variability whenever disclosed herein whether the word "about" is present or not.

Variability also exists in thermal measurements, such as DSC, and may also be indicative of sample purity. Melting point, DSC, and hot stage microscopy, alone or in combination with techniques such as x-ray powder diffraction, Raman spectroscopy, infrared spectroscopy or some combination thereof, may be used to characterize cocrystals. With respect to DSC, typical measurement variability is on the order of 1° C. However, with regards to fasoracetam, due to the low melting behavior and interactions with water, DSC measurements are reported herein for fasoracetam-containing materials to within 3° C.

SUMMARY

In one aspect of the disclosure, Form II R-fasoracetam monohydrate is provided.

In another aspect of the disclosure, anhydrate R-fasoracetam is provided.

In a further aspect of the disclosure, a mixture of R-fasoracetam forms is provided.

Definitions

"Fasoracetam" as used herein means R-fasoracetam unless otherwise stated:

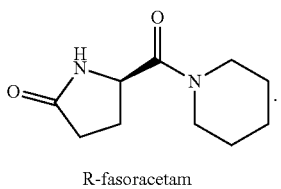 [SMILES: O=C1CC[C@H](C(=O)N2CCCCC2)N1]

R-fasoracetam

"R-Fasoracetam Forms Mixture" means a mixture of R-fasoracetam monohydrate Form I, R-fasoracetam monohydrate Form II, and R-fasoracetam anhydrate. This mixture of fasoracetam forms can be prepared, for example in accordance with Example 2.

"Form I" means R-fasoracetam monohydrate Form I.

"Form II" means R-fasoracetam monohydrate Form II.

"Anhydrate form" means the anhydrate form of R-fasoracetam.

"Match" means that to one of ordinary skill in the art, two analytical responses, typically XRPD patterns are the same to within normal expected variability. With respect to the matching analysis, x-axis alignment is significantly more important than y-axis alignment in XRPD patterns due to preferred orientation of crystals and particle statistics.

DESCRIPTION

Figure 1:
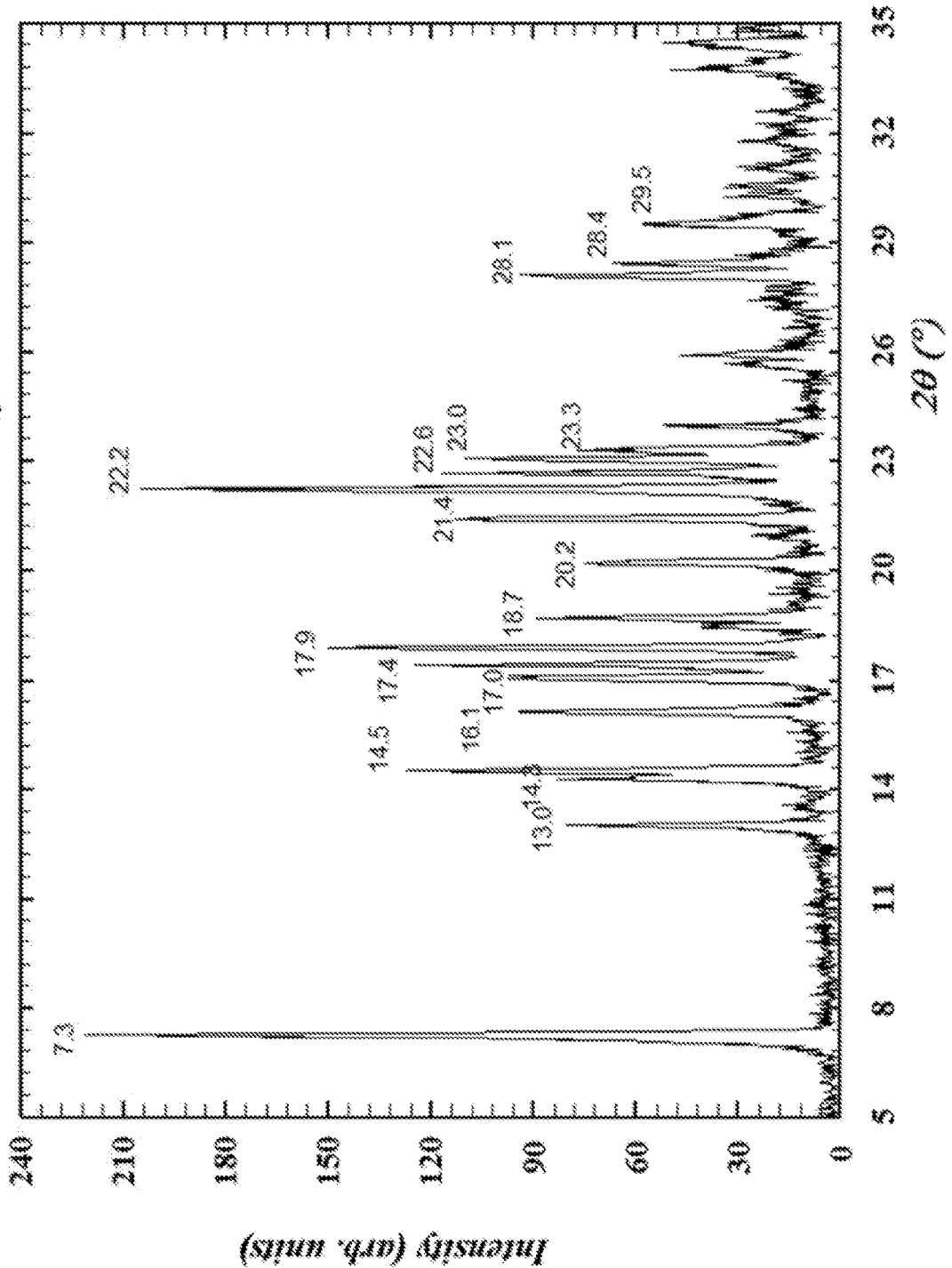
FIG. 1 is an XRPD pattern of R-fasoracetam monohydrate Form I.
Figure 4:
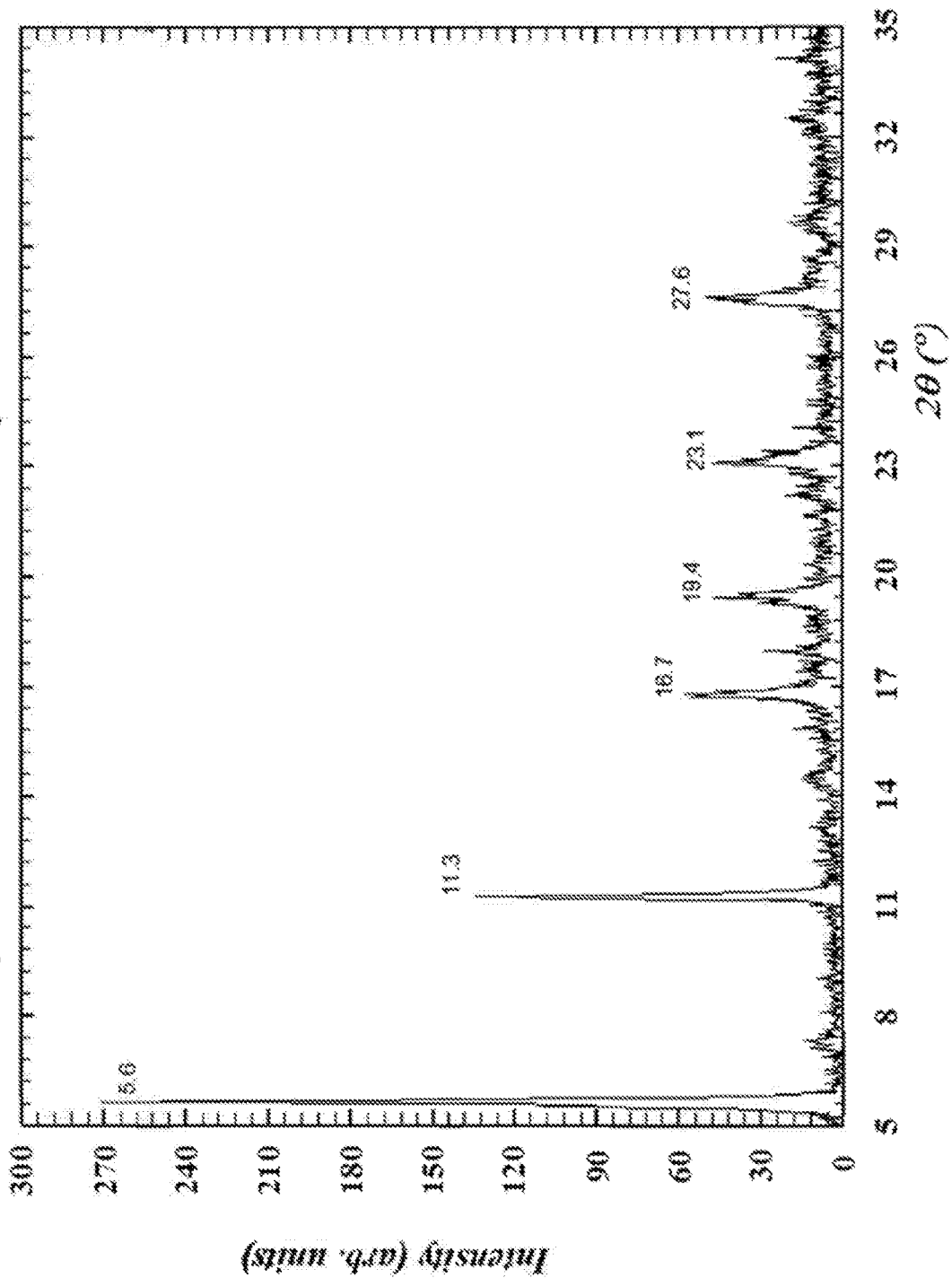
FIG. 4 is an XRPD pattern of R-fasoracetam monohydrate Form II.
Figure 6:
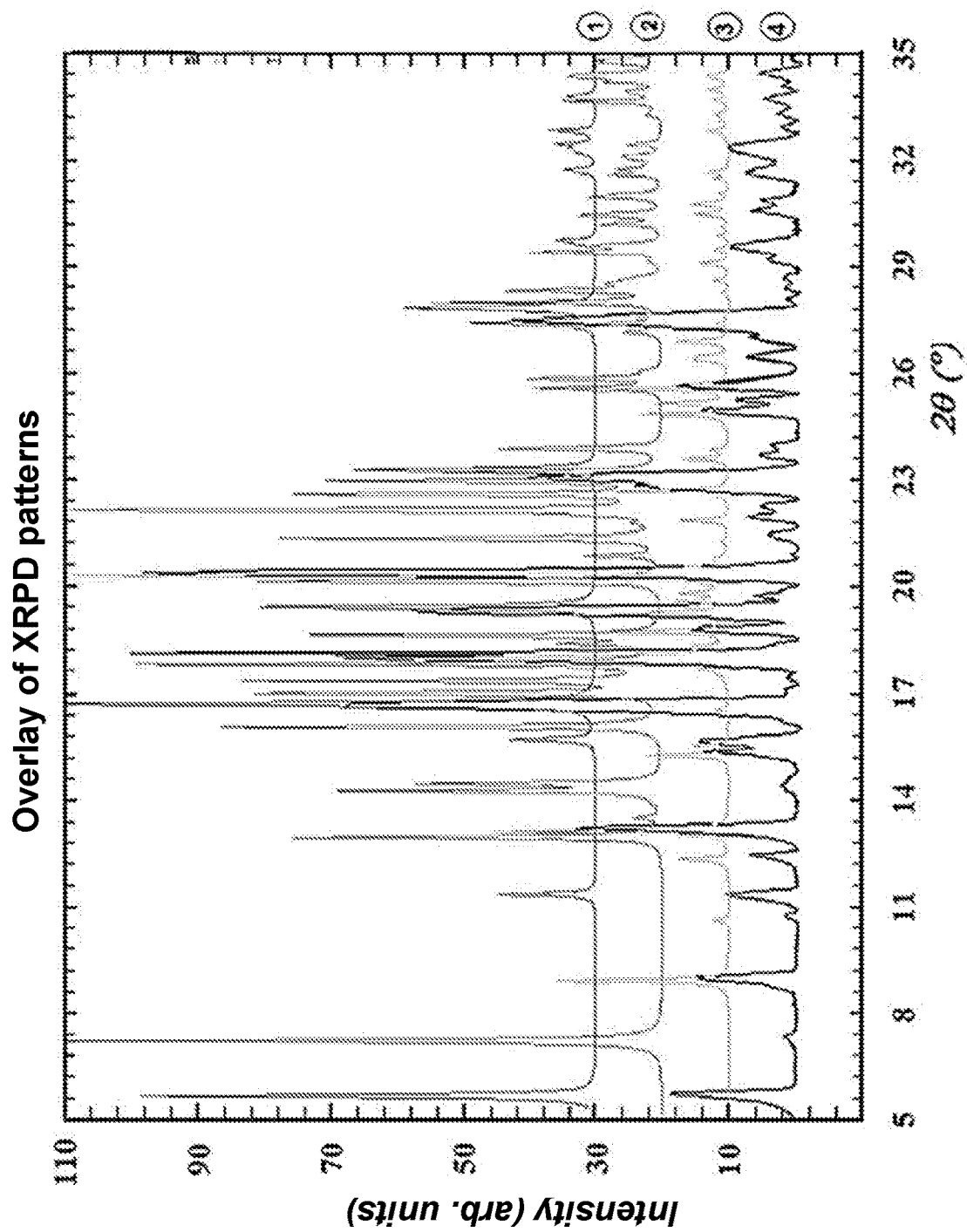
FIG. 6 is an overlay of XRPD patterns: (1) R-fasoracetam monohydrate Form II simulated; (2) R-fasoracetam monohydrate Form I simulated; (3) anhydrate R-fasoracetam simulated; (4) Mixture of R-fasoracetam monohydrate Form I, R-fasoracetam monohydrate Form II, and anhydrate R-fasoracetam.

In various embodiments of the disclosure, R-fasoracetam monohydrate Form II is provided. This Form II is a polymorph of R-fasoracetam monohydrate Form I in that it has the same chemical composition, but differs in crystal structure. FIG. 4 is an XRPD pattern of R-fasoracetam monohydrate Form II and FIG. 1 is an XRPD pattern of R-fasoracetam monohydrate Form I. FIG. 6 is an overlay XRPD pattern showing the XRPD pattern overlays of Form I, Form II, the anhydrate form of R-fasoracetam, and a mixture thereof. As can be seen from these figures, Form II is clearly distinguishable from Form I and the anhydrate. This is confirmed because each of these three solid forms has a different single crystal structure.

Form II of R-fasoracetam monohydrate can be characterized by one or more XRPD peaks at about 5.7°2θ, about 11.3°2θ, and about 19.4°2θ. There are no peaks at such angles, to within expected variability, in the XRPD pattern of Form I. In addition, one or more of the peaks above may be characterized together with one or more peaks at about 16.7°2θ, and about 23.3°2θ.

Form II of R-fasoracetam monohydrate is further characterized by an onset melting point temperature of about 49° C. with or without one or more of the XRPD peaks at about 5.7°2θ, about 11.3°2θ, and about 19.4°2θ. Additional peaks, such as those at about 16.7°2θ, and about 23.3°2θ may be used to characterize Form II. Form II may be characterized by a diffraction pattern substantially the same as that of FIG. 11 and/or a DSC thermogram substantially the same as that of FIG. 5.

Figure 12:
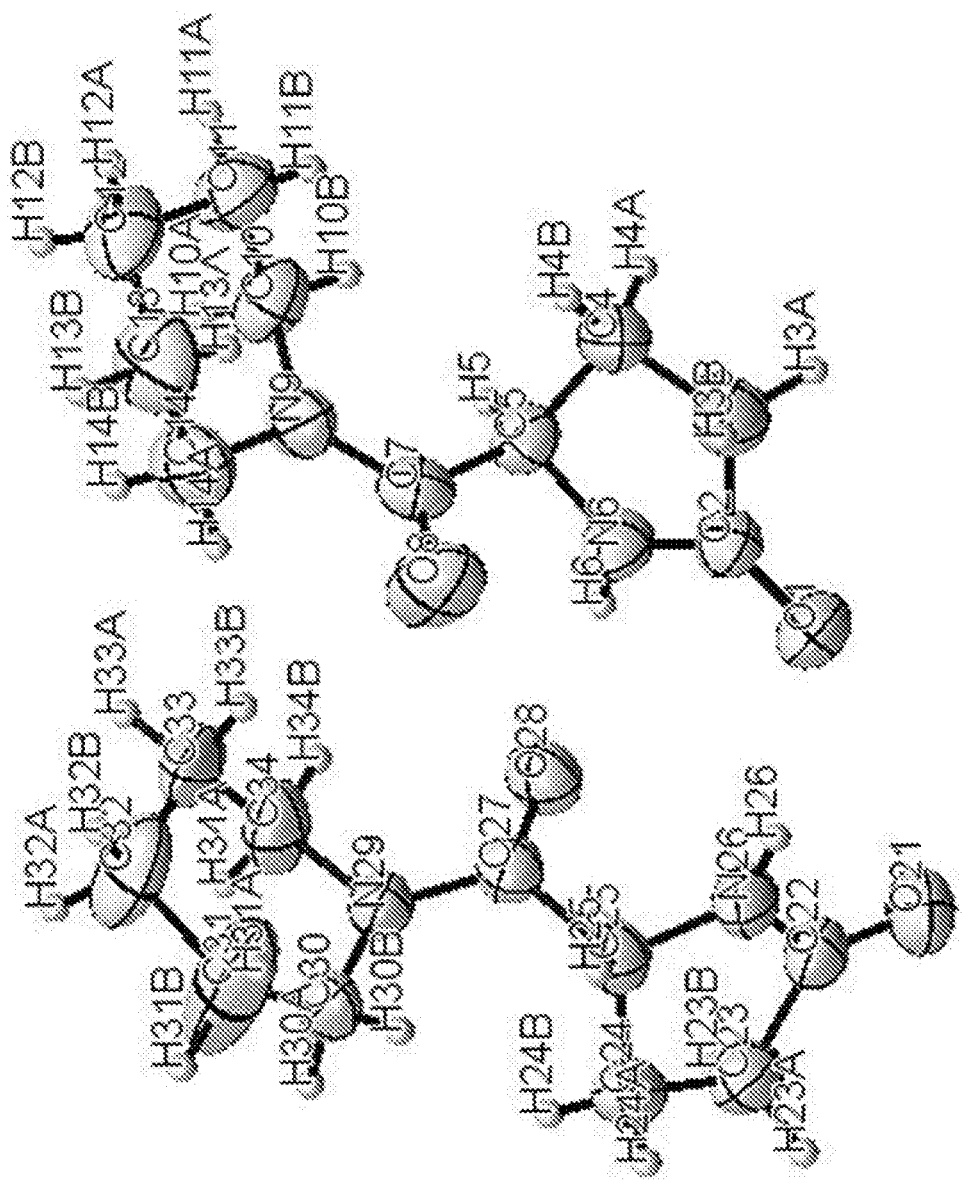
FIG. 12 is an ORTEP drawing of R-fasoracetam anhydrate.
Figure 13:
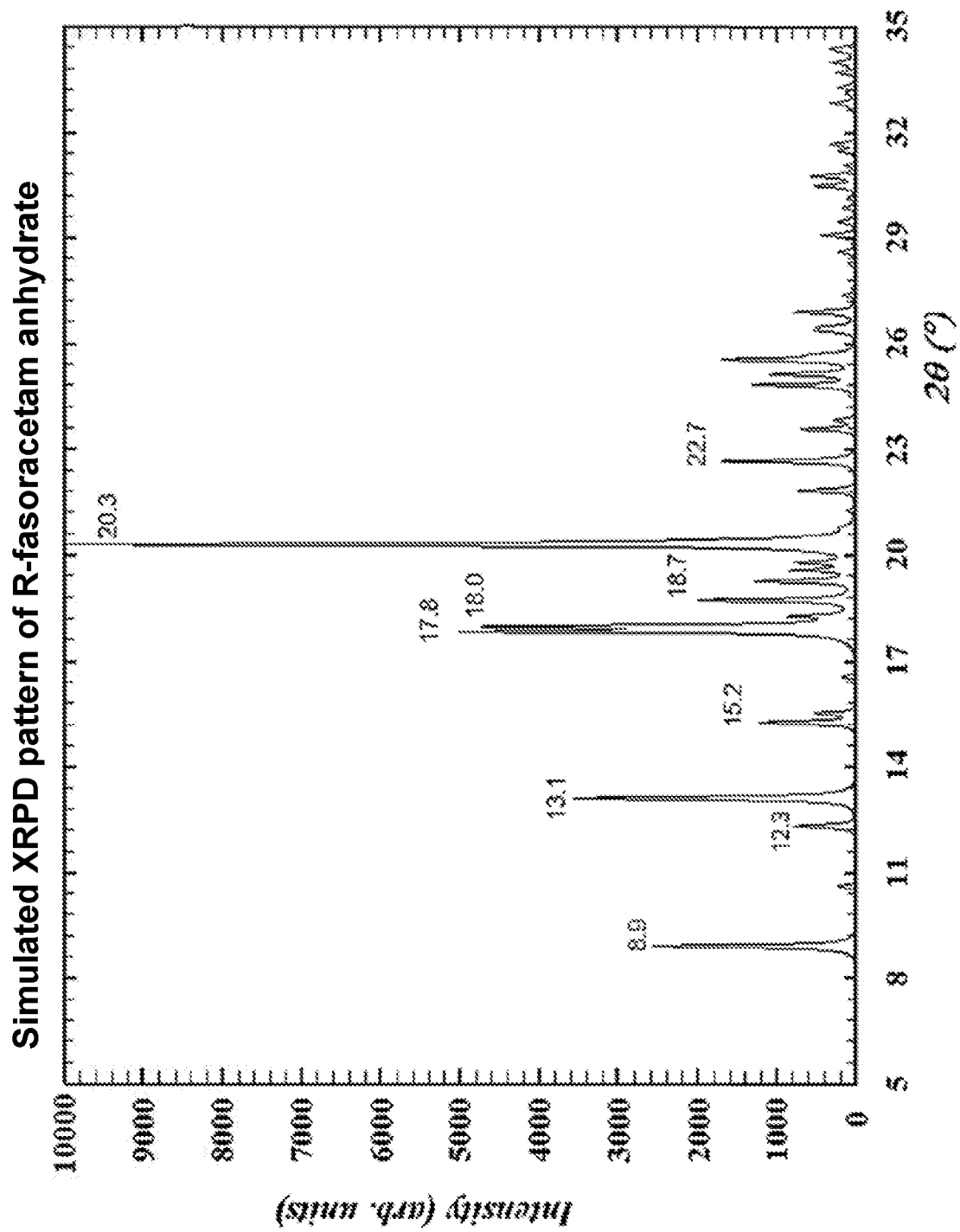
FIG. 13 is a simulated XRPD pattern of R-fasoracetam anhydrate.
Figure 25:
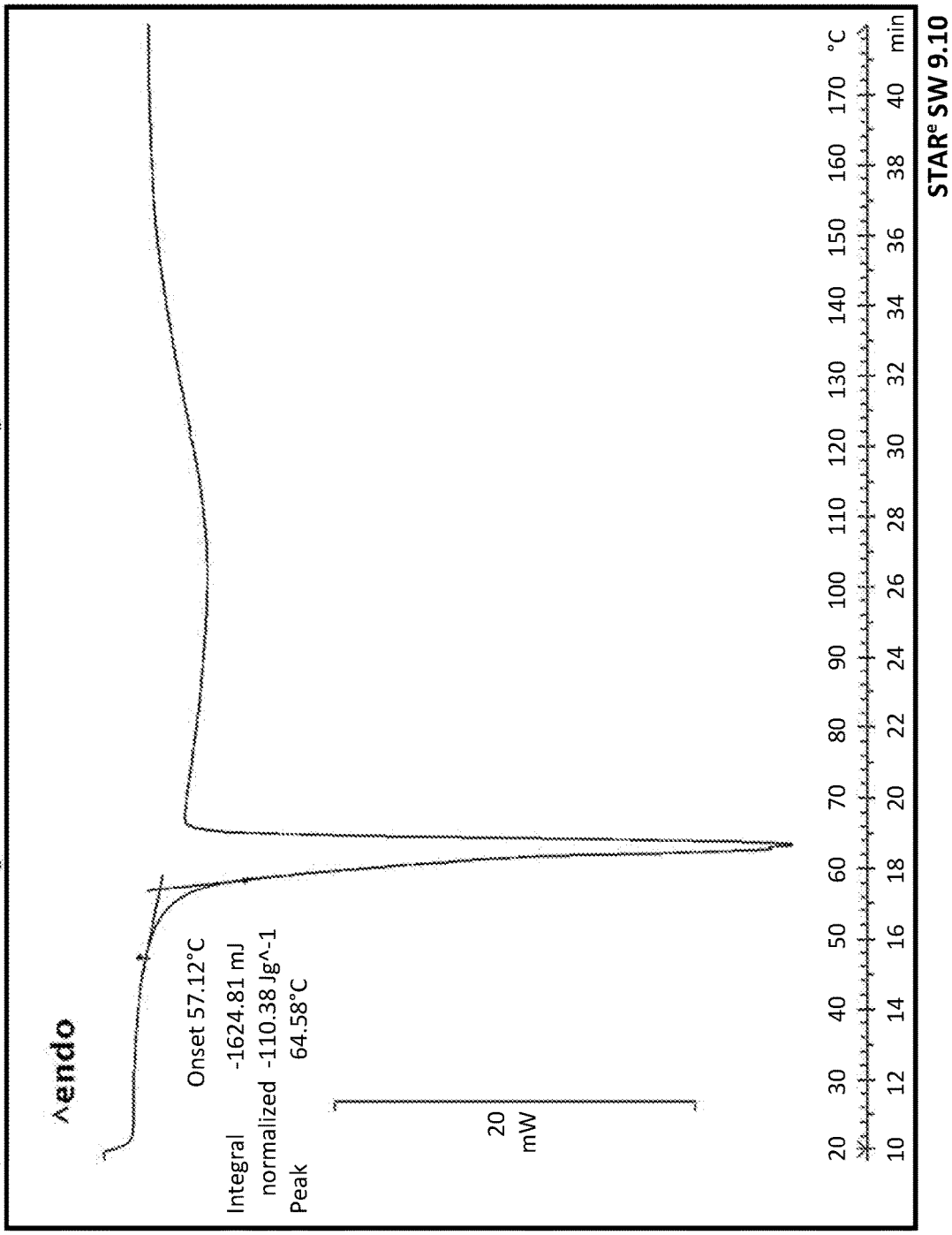
FIG. 25 is a DSC thermogram of R-fasoracetam anhydrate at 10° C./minute.

In further embodiments of the disclosure, R-fasoracetam anhydrate is provided. The anhydrate differs from R-fasoracetam monohydrate Forms I and II in that it lacks water of crystallization as seen in its ORTEP single-crystal representation in FIG. 12. This lack of water of crystallization is a characterizing feature of the anhydrate of R-fasoracetam with respect to Form I or Form II. FIG. 13 is an XRPD pattern of the anhydrate and any one or more of the peaks in that XRPD pattern may be used to characterize the anhydrate. Thus, one or more peaks at about 8.9°2θ, about 13.1°2θ, about 15.2°2θ, about 17.8°2θ, about 18.7°2θ, about 20.3°2θ, and about 22.7°2θ may be used to characterize the anhydrate form of R-fasoracetam. The anhydrate has an onset melting temperature at about 94° C. Thus, in another embodiment, an onset melting point of about 94° C. together with one or more peaks at about 8.9°2θ, about 13.1°2θ, about 15.2°2θ, about 17.8°2θ, about 18.7°2θ, about 20.3°2θ, and about 22.7°2Θ may be used to characterize R-fasoracetam anhydrate. R-fasoracetam anhydrate may be further characterized by a diffraction pattern substantially the same as that of FIG. 13. A DSC thermogram of R-fasoracetam anhydrate appears in FIG. 25. The ramp rate was at 10° C. per minute. The R-fasoracetam anhydrate being hygroscopic, the sample in FIG. 25 was obtained by keeping R-fasoracetam monohydrate Form I under vacuum for a prolonged period at a temperature of 65° C.

In additional embodiments, a mixture of Form I, Form II, and anhydrate R-fasoracetam is provided. For example, a mixture of fasoracetam Forms was prepared in Example 2. The mixture may be prepared, for example, by melting Form I and then recrystallizing by cooling. This mixture contains R-fasoracetam Form I, Form II, and the anhydrate form and FIG. 6 shows the XRPD pattern of that mixture compared with the simulated pattern of the component parts. With a single crystal x-ray solution, one may also calculate what is called a "simulated" x-ray powder diffraction ("XRPD") pattern using techniques well known in the art.

The XRPD pattern of the mixture is a linear combination of the pure simulated patterns (with varying intensities) which indeed confirms a mixture is present. For example, considering the first 7 peaks of the mixture's diffraction pattern, those peaks each correspond to a peak in one of the simulated patterns. The peaks at about 5.7°2θ and about 11.3°2θ correspond to Form II. The peak at about 7.2°2θ corresponds to Form I, and the peaks at about 8.9°2θ, about 12.3°2θ, and about 13.1°2θ correspond to the anhydrate. The peak at about 12.9°θ corresponds to Form I, but is also close to the 13.1°2θ in the anhydrate. Nevertheless, these two peaks between about 12.9°2θ and about 13.1°2θ are accounted for by Form I and the anhydrate. It is also worth noting that the general intensity of the Form I peaks at angles under about 14°2θ are much weaker than Form II and the anhydrate form. The simulated XRPD patterns can be found at FIGS. 16 (R-fasoracetam Form I), 11 (R-fasoracetam Form II), and 13 (anhydrate R-fasoracetam). Thus, for example, a mixture of fasoracetam Forms may be characterized by peaks at about 5.7°2θ, about 7.2°2θ, and about 12.9°2θ. The Forms may also be characterized by peaks at about 5.7°2θ or about 11.3°2θ or both, and about 7.2°2θ, and one or more of the peaks about 8.9°2θ, about 12.3°2θ, and about 13.1°2θ.

The R-fasoracetam Forms Mixture may also be characterized by an onset melting temperature, such as at about 93.5° C., likely corresponding to the melting of the anhydrate present. The endotherm melts at about 54.5° C. likely corresponds to Form I. In addition to a Forms Mixture, a preparation of a mixture of anhydrate R-fasoracetam with either Form I R-fasoracetam or Form II R-fasoracetam following the general procedures of Example 2. Thus, one may prepare a mixture that has only one of the monohydrate polymorphic forms of R-fasoracetam and the anhydrate.

The fasoracetam forms mixture is useful in delivering fasoracetam as a starting material, such as in crystallization experiments to make cocrystals, where it is desirable to limit the amount of water used. Although pure anhydrate fasoracetam is drier than the mixture, it is difficult to prepare and maintain pure anhydrate fasoracetam without at least some conversion to the monohydrate.

This disclosure also relates to pharmaceutical compositions containing solid forms or crystalline compounds of fasoracetam as disclosed herein. Such pharmaceutical compositions are comprised of one or more pharmaceutically acceptable excipients and a solid form or crystalline material of the disclosure. Such pharmaceutical compositions may be administered orally or configured to be delivered as any effective conventional dosage unit forms, including immediate, slow and timed release oral preparations, parenterally, topically, nasally, ophthalmically, optically, sublingually, rectally, vaginally, and the like.

Figure 2:
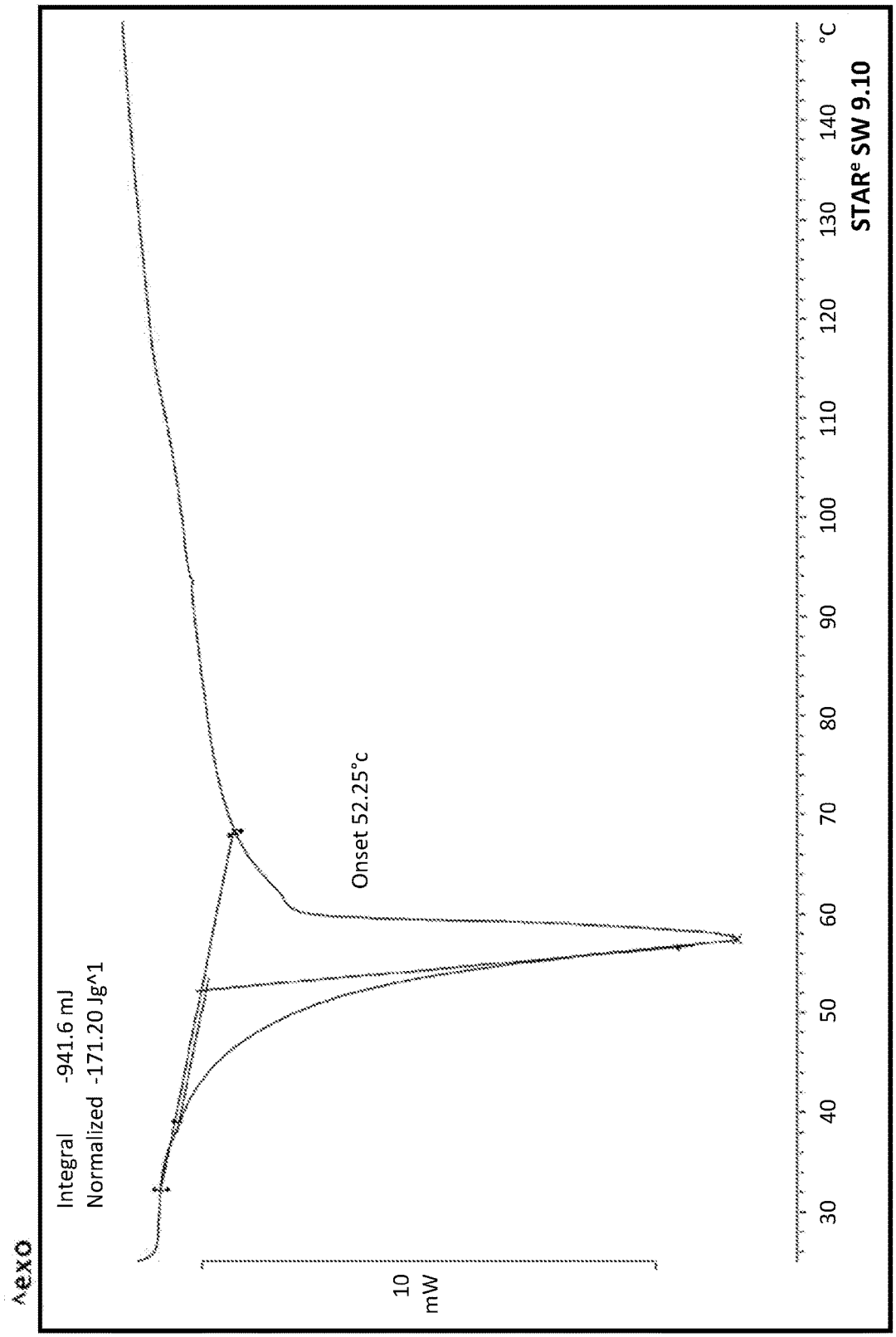
FIG. 2 is a DSC thermogram of R-fasoracetam monohydrate Form I.
Figure 3:
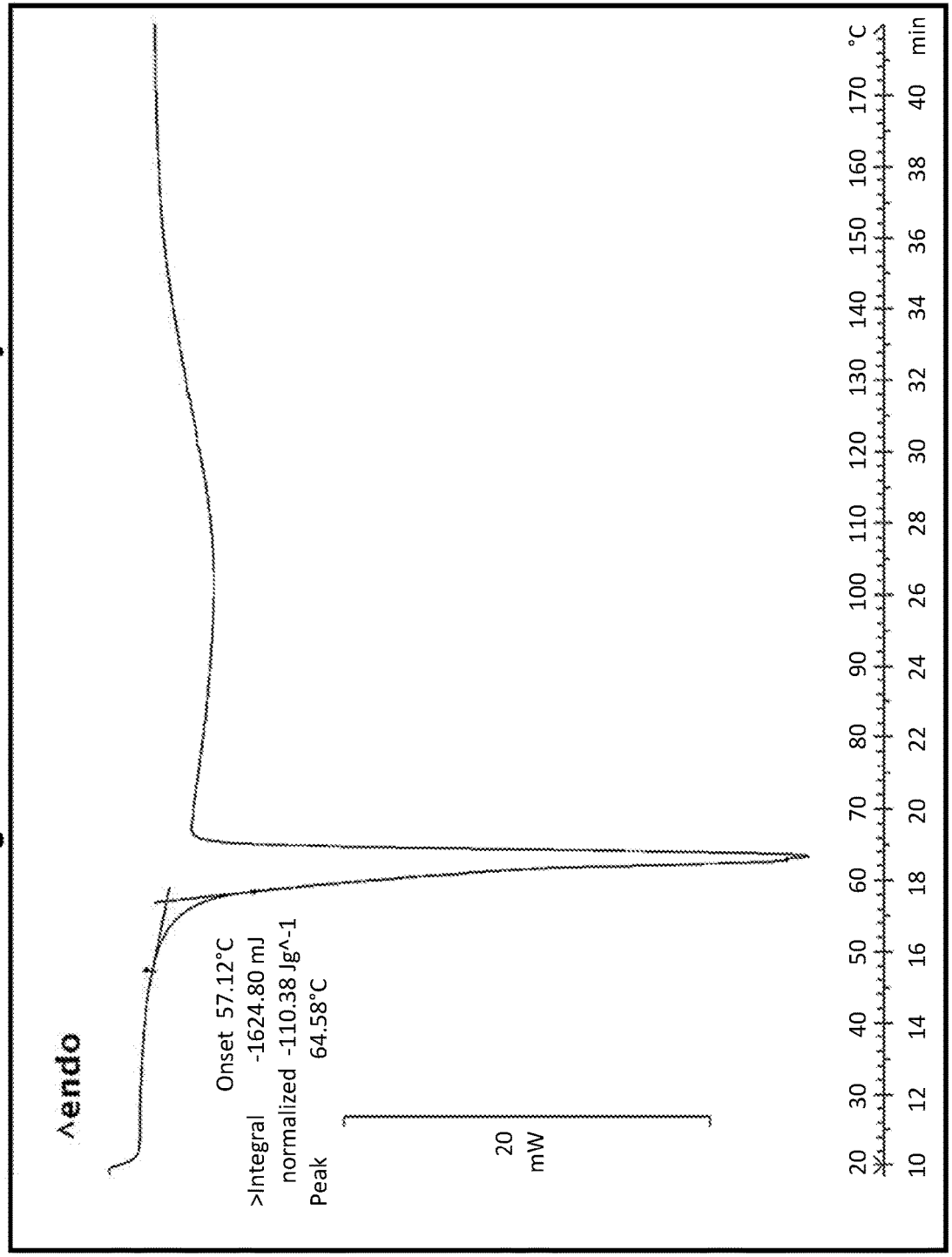
FIG. 3 is a DSC thermogram of R-fasoracetam monohydrate Form I stored under drier conditions compared to ambient conditions.

The disclosure further includes methods and uses for treating diseases in humans such as ADHD, 22q11.2 deletion syndrome, anxiety, conduct disorder, Tourette's syndrome, and anorexia with effective amount of cocrystals, crystalline compounds, and/or pharmaceutical compositions comprising the cocrystals and/or crystalline compounds of fasoracetam of the disclosure. In some embodiments, the subject with ADHD, 22q11.2 deletion syndrome, anxiety, conduct disorder, Tourette's syndrome, or anorexia has at least one has at least one copy number variation (CNV) in a metabotropic glutamate receptor (mGluR) network gene (see, e.g., FIGS. 1-3 of WO2017/044491). In some embodiments, the mGluR network gene selected from GRM5, GRM8, GRM7, GRM1, NEGR1, SGTB/NLN, USP24, CNTN4, CTNNA2, LARP7, MC4R, SNCA, CA8.

The following numbered embodiments are contemplated and are non-limiting:

Clause 1. A mixture of Form I, Form II, and anhydrate R-fasoracetam.

Clause 2. A mixture of anhydrate R-fasoracetam and Form I or Form II R-fasoracetam.

Clause 3. The mixture of clause 1, prepared my melting and recrystallizing Form I of R-fasoracetam.

Clause 4. The mixture of clause 3, wherein the melting was done under partial vacuum.

Clause 5. The mixture of any one of clauses 1, or 3-4, wherein the mixture has an x-ray powder diffraction pattern comprising one or more peaks chosen from peaks at about 5.7°2Θ, about 7.2°2Θ, and about 12.9°2Θ.

Clause 6. The mixture of any one of clauses 1, or 3-4, wherein the mixture has an x-ray powder diffraction pattern comprising one or more peaks chosen from peaks at about 5.7°2Θ or about 11.3°2Θ or both, and about 7.2°2Θ, and one or more of the peaks about 8.9°2Θ, about 12.3°2Θ, and about 13.1°2Θ.

Clause 7. The mixture of any one of clauses 1-6, having at least two melting events.

Clause 8. The mixture of clause 7, wherein one onset melting temperature is at about 93.5° C.

Clause 9. The mixture of clauses 7 or 8 wherein the melting is measured by DSC.

Clause 10. Form II monohydrate R-fasoracetam.

Clause 11. The Form II monohydrate R-fasoracetam of clause 10, wherein Form II has an x-ray powder diffraction pattern comprising by one or more XRPD peaks chosen from peaks at about 5.7°2Θ, about 11.3°2Θ, and about 19.4°2Θ.

Clause 12. The Form II monohydrate R-fasoracetam of clause 11, wherein Form II has an x-ray powder diffraction pattern comprising a peak at about 5.7°2Θ.

Clause 13. The Form II monohydrate R-fasoracetam of clause 11, wherein Form II has an x-ray powder diffraction pattern comprising a peak at about 11.3°2Θ.

Clause 14. The Form II monohydrate R-fasoracetam of clause 11, wherein Form II has an x-ray powder diffraction pattern comprising a peak at about 19.4°2Θ.

Clause 15. The Form II monohydrate R-fasoracetam of any one of clauses 11-14, wherein Form II has an x-ray powder diffraction pattern further comprising one or more peaks chosen from peaks at about 16.7°2Θ and about 23.3°2Θ.

Clause 16. The Form II monohydrate R-fasoracetam of any one of clauses 10-15, wherein Form II has an onset melting temperature of about 49° C.

Clause 17. Form II monohydrate having an x-ray powder diffraction pattern substantially the same as FIG. 11.

Clause 18. Form II monohydrate having a DSC thermogram substantially the same as FIG. 5.

Clause 19. Anhydrate R-fasoracetam.

Clause 20. The Anhydrate R-fasoracetam of clause 19, wherein the Anhydrate has an x-ray powder diffraction pattern comprising one or more peaks chosen from peaks at about 8.9°2Θ, about 13.1°2Θ, about 15.2°2Θ, about 17.8°2Θ, about 18.7°2Θ, about 20.3°2Θ, and about 22.7°2Θ.

Clause 21. The Anhydrate R-fasoracetam of clause 19, wherein the Anhydrate has an x-ray powder diffraction pattern comprising a peak at about 8.9°2Θ.

Clause 22. The Anhydrate R-fasoracetam of clause 19, wherein the Anhydrate has an x-ray powder diffraction pattern comprising a peak at about 13.1°2Θ.

Clause 23. The Anhydrate R-fasoracetam of clause 19, wherein the Anhydrate has an x-ray powder diffraction pattern comprising a peak at about 15.2°2Θ.

Clause 24. The Anhydrate R-fasoracetam of clause 19, wherein the Anhydrate has an x-ray powder diffraction pattern comprising a peak at about 17.8°2Θ.

Clause 25. The Anhydrate R-fasoracetam of clause 19, wherein the Anhydrate has an x-ray powder diffraction pattern comprising a peak at about 18.7°2Θ.

Clause 26. The Anhydrate R-fasoracetam of clause 19, wherein the Anhydrate has an x-ray powder diffraction pattern comprising a peak at about 20.3°2Θ.

Clause 27. The Anhydrate R-fasoracetam of clause 19, wherein the Anhydrate has an x-ray powder diffraction pattern comprising a peak at about 22.7°2Θ.

Clause 28. The Anhydrate R-fasoracetam of any one of clauses 19-27, wherein the Anhydrate has an onset melting temperature of about 94° C.

Clause 29. Anhydrate R-fasoracetam having an x-ray powder diffraction pattern substantially the same as FIG. 13.

EXAMPLES

Materials and Methods

Fasoracetam was ordered from Jinan HaoHua Industry Co., Ltd., and used as received. It was identified via X-ray powder diffraction to be the most stable form of the hydrate (hydrate I).

All solvents used were obtained from VWR International S.A.S. and used without further purification.

Instrument Settings

Two X-ray powder diffraction (XRPD) devices were used to analyze the samples reported herein. Some samples were measured with a Siemens D5000 diffractometer equipped with a Cu X-ray source operating at 40 kV and 40 mA and a secondary monochromator allowing to select the Kα radiation of Cu ($\lambda=1.5418$ Å). A scanning range of 2θ values from 2° to 50°.

Other samples were analyzed with a PANalytical Bragg-Brentano-geometry diffractometer, using Ni-filtered Cu Kα radiation ($\lambda=1.54179$ Å) at 40 kV and 40 mA with a X'Celerator detector. On this instrument, samples were analyzed between 4 and 50° in 2θ.

Peak picking was performed using the WinPLOTR tool available in the commercially available crystallographic tool software known as "FullProf Suite." Most peak picking was performed using the automatic peak search option with its predefined defaults while some peaks were selected manually.

DSC measurements were performed on a DSC 821 METTLER TOLEDO under continuous nitrogen flow. Perforated aluminium crucibles were used for analysis. Onsets were determined by manually constructing a tangent to the peak and a prolongation of the baseline. Total enthalpies were calculated by manual peak integration using a linear interpolation between the initial and final temperatures of integration. To obtain the normalized enthalpy, the total enthalpy was divided by the total sample mass. Ramp rates were typically done at 5° C./minute TGA measurements were carried out on a METTLER TOLEDO TGA/SDTA 851e. Samples were placed in open aluminum oxide crucible. All experiments were performed under nitrogen flow.

$^1$H-NMR spectra were recorded on Bruker-300. $^1$H-NMR chemical shifts are reported relative to $(CD_3)_2SO$ (2.5 ppm) or $CD_3OD$ (3.3 ppm).

Single crystal X-ray diffraction was performed on a MAR345 detector using monochromated Mo Kα radiation ($\lambda=0.71073$ Å)(Xenocs Fox3D mirror) produced by a Rigaku UltraX 18 generator. The data images were integrated by CrysAlisPRO and the implemented multiscan absorption applied. In some cases, an analytical numeric absorption correction was also applied. The structures were solved with SHELXT and then refined on $|F^2|$ using SHELXL-2014/7 or SHELXL-2018/1. Nonhydrogen atoms were anisotropically refined.

Hydrogen atoms were typically placed in the riding mode with isotropic temperature factors fixed at 1.2 times U(eq) of the parent atoms (1.5 times for methyl groups). Simulated XRPD patterns were calculated from the single crystal structures using the Mercury 3.3 program. For the anhydrate structure, the piperidine rings were found to be disordered with the minor fraction<10%. The minor part was restrained to be similar (bond and angles) to the main fraction.

The single crystals obtained for SC-XRD analysis were grown via different methods. Initially, fasoracetam (as received, hydrate form I) was recrystallized from water using solvent evaporation. The second hydrate, form II, is less stable and was obtained from methanol evaporation, which provided large enough single crystals. The anhydrate form could not be crystallized from any of the solvents used. To obtain this form, a recrystallization from the melt was performed in vacuo, where it was kept at 60° C. for 1 week. These conditions allowed water to be removed from the melt. After a 1-week period the temperature was lowered while maintaining vacuum conditions, which resulted in a different solid form, the anhydrate, with crystals suitable for SC-XRD analysis. Starting from hydrates I and II, both convert into the same anhydrated form using the method described above.

Example 1

Preparation of R-Fasoracetam Monohydrate Form II

Figure 5:
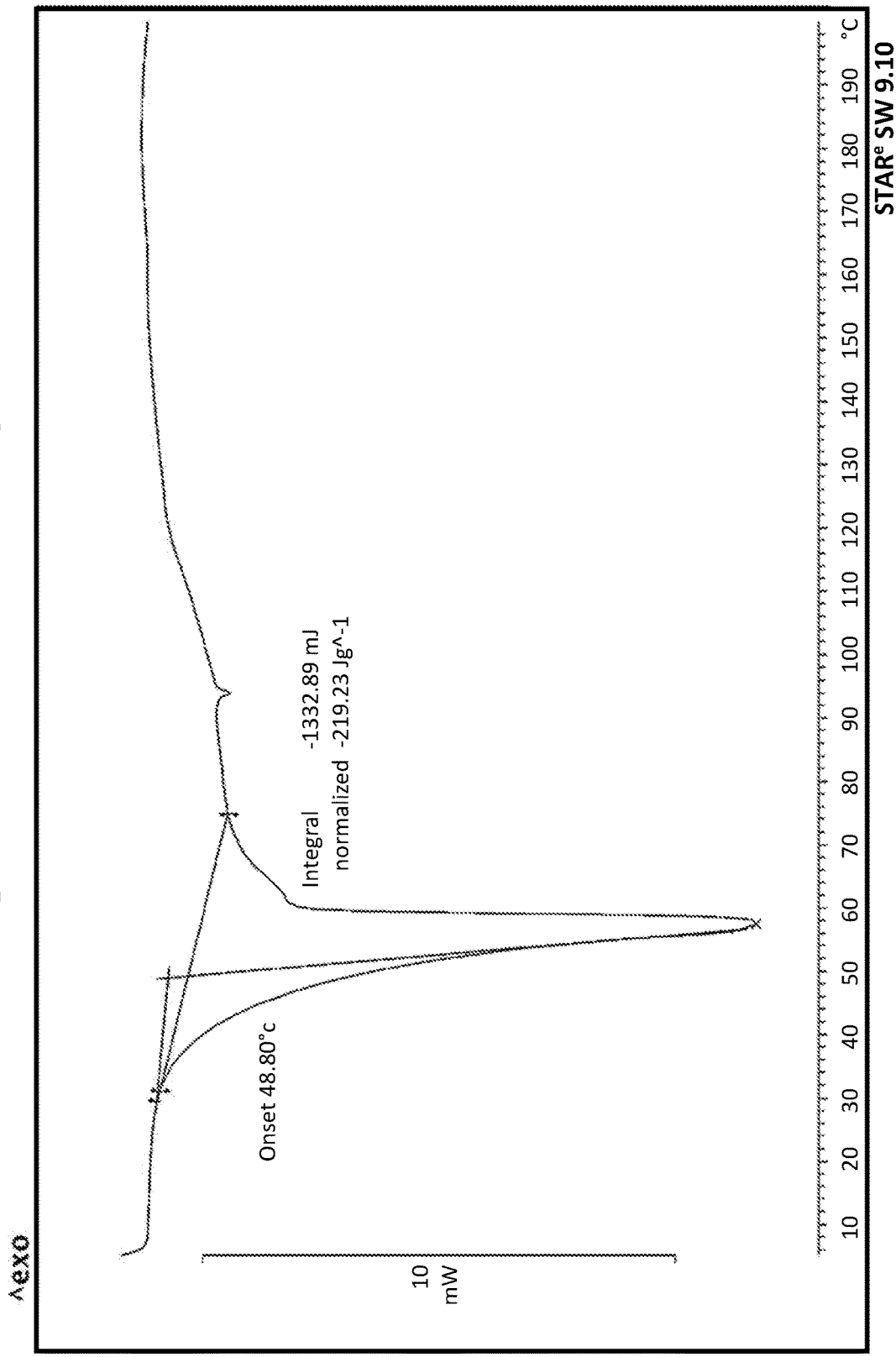
FIG. 5 is a DSC thermogram of R-fasoracetam monohydrate Form II.

R-fasoracetam monohydrate Form II was obtained by adding water to 50.69 mg of R-fasoracetam monohydrate Form I (from Aevi Genomics) until total dissolution occurred. The solution was then left to evaporate at room temperature for 21 days after which a crystalline powder was obtained, for which the powder pattern is shown in FIG. 4, which contains R-fasoracetam monohydrate Form II and a small amount of Form I. FIG. 5 is a DSC thermogram of R-fasoracetam monohydrate Form II containing a small amount of Form I.

Example 2

Preparation of R-Fasoracetam Forms Mixture and Anhydrate

R-fasoracetam monohydrate Form I was sourced from Jinan Haohua Industry Co., Ltd. and was placed in a round bottom flask and rotavapped for 30 min at 65° C. This procedure has been performed multiple times. In some cases, melting was observed, followed by recrystallization at 65° C. where the recrystallized material is the anhydrate R-fasoracetam. In others, there was no recrystallization at 65° C. and recrystallization only occurred when the temperature was lowered. In those cases, Form I and/or Form II may also crystallize when the melt is taken below the melting points of those forms. The x-ray powder diffraction pattern of the resulting solid typically shows a Fasoracetam Forms Mixture of both Form I and Form II as well as the anhydrate form of R-fasoracetam. FIG. 6 shows an overlay of diffraction patterns of the simulated patterns from single crystal solutions of the component R-fasoracetam forms compared with the experimental diffraction pattern of the Fasoracetam Forms Mixture.

Figure 7:
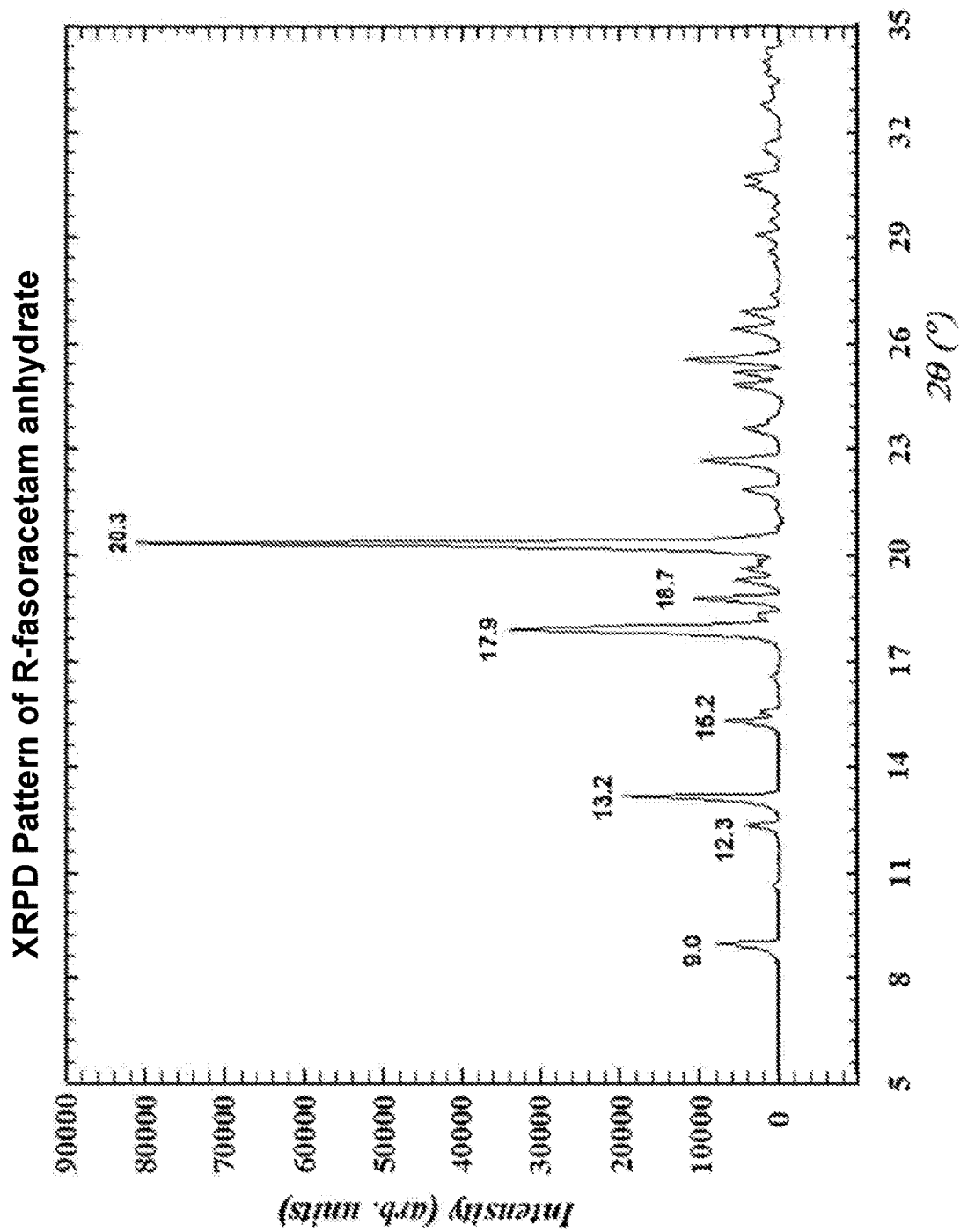
FIG. 7 is an XRPD pattern of R-fasoracetam anhydrate.
Figure 8:
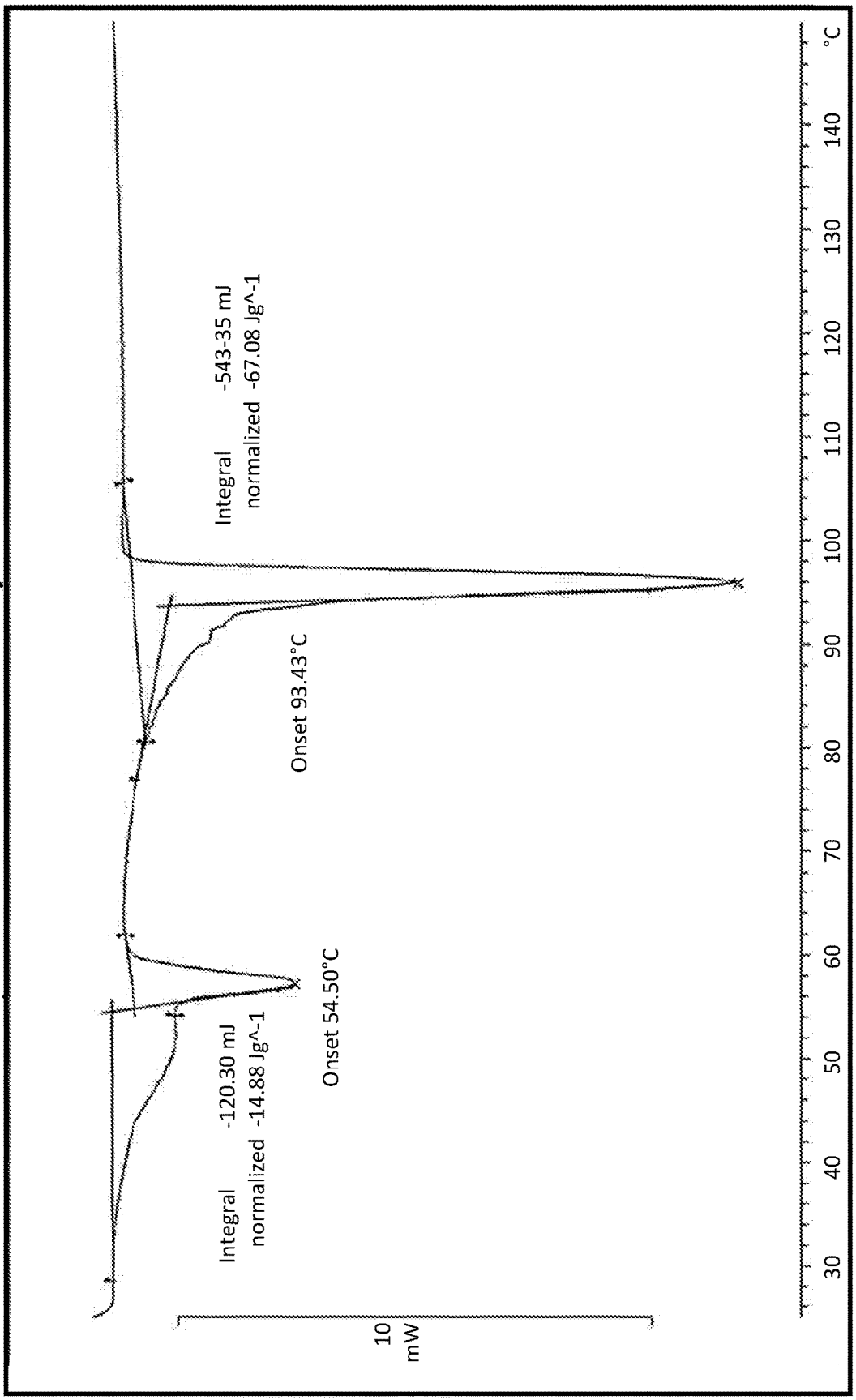
FIG. 8 is a DSC thermogram of the mixture of R-fasoracetam monohydrate Form I, R-fasoracetam monohydrate Form II, and R-fasoracetam anhydrate.

To measure the x-ray powder diffractogram of R-fasoracetam anhydrate, the mixture was placed at 80° C. At that temperature, only the pattern of the anhydrate remains, as shown in FIG. 7. FIG. 8 is a DSC thermogram of the mixture of R-fasoracetam monohydrate Form I, R-fasoracetam monohydrate Form II, and R-fasoracetam anhydrate. The thermogram shows an onset temperature of about 93.5° C., likely corresponding to the melting of the anhydrate present. The endotherm starting with a shoulder at about 46° C. is likely due to the presence of R-fasoracetam monohydrate Form I and/or R-fasoracetam monohydrate Form II.

Example 3

Single Crystal Preparation of R-Fasoracetam Monohydrate Form II

Figure 9:
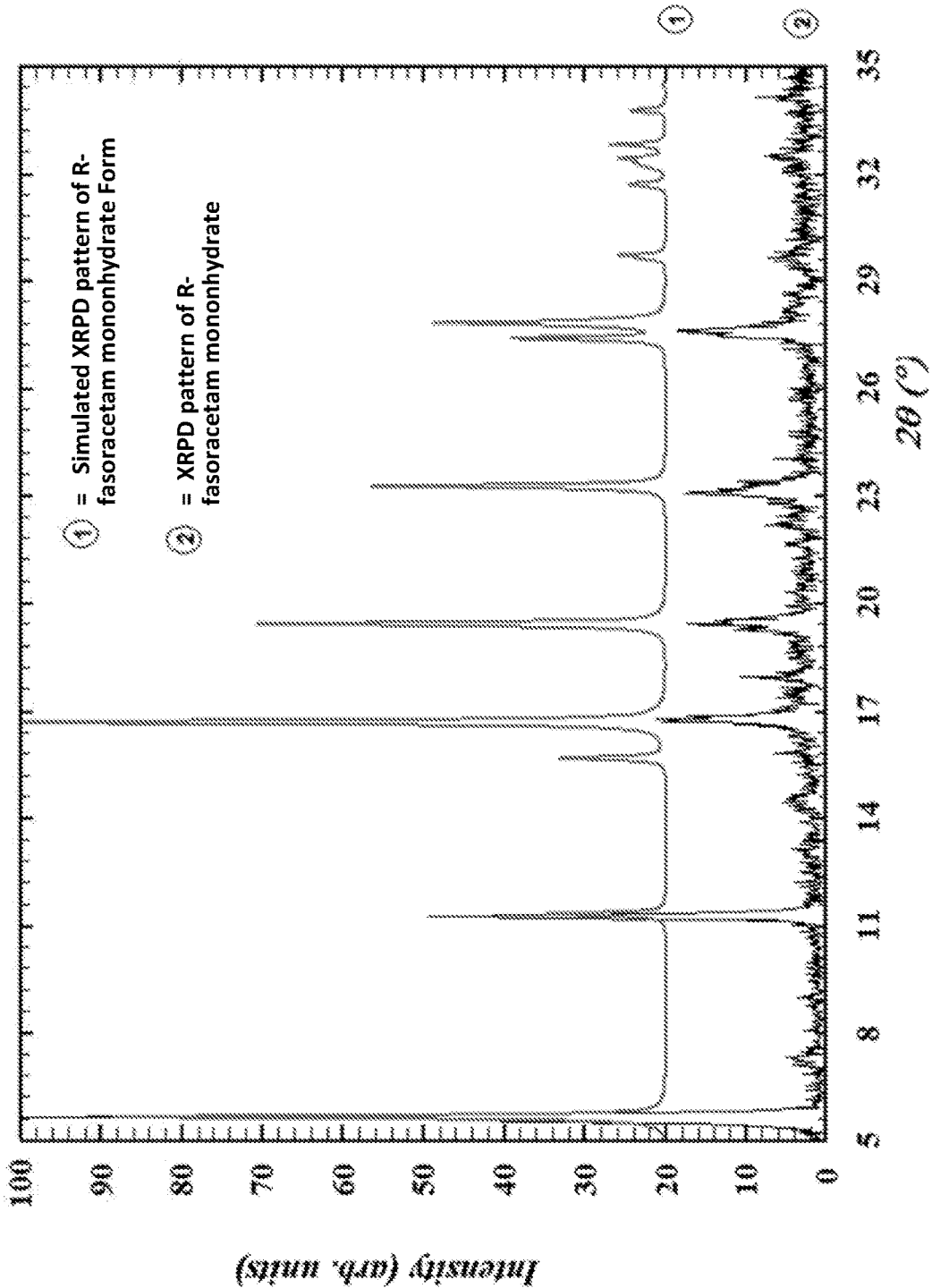
FIG. 9 is an overlay of XRPD patterns: (1) Simulated XRPD pattern of R-fasoracetam mononhydrate Form II; (2) XRPD pattern of R-fasoracetam mononhydrate Form II.
Figure 10:
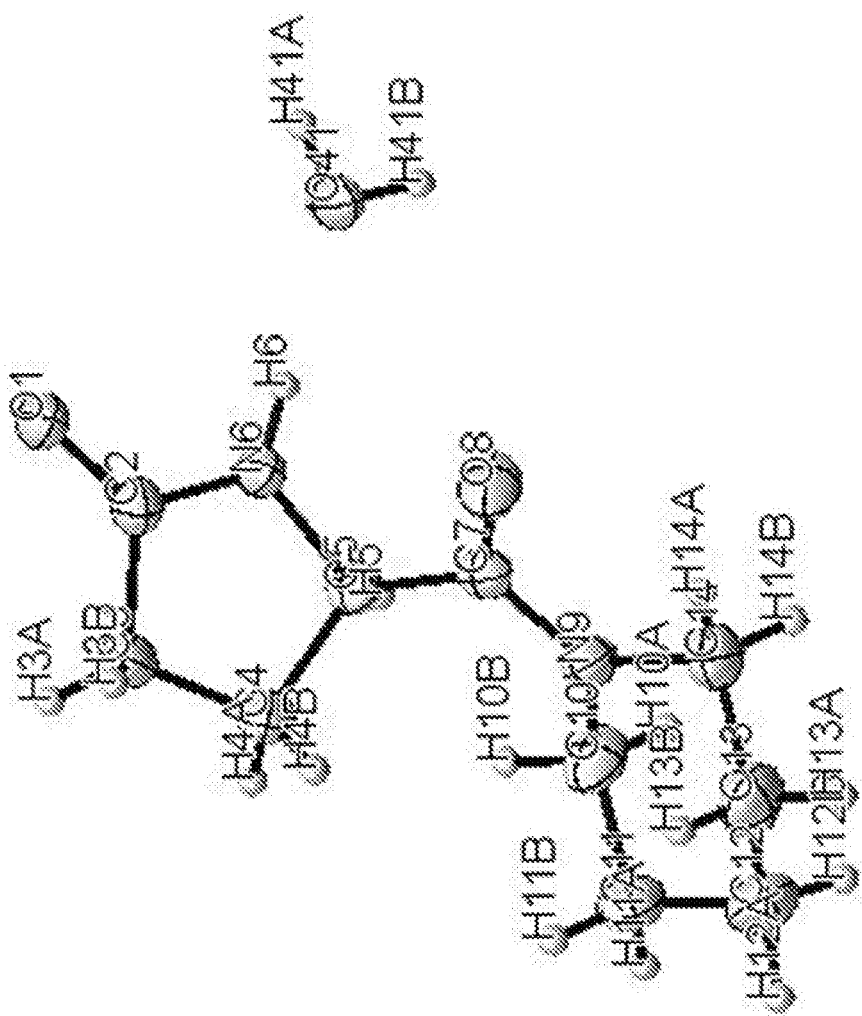
FIG. 10 is an ORTEP drawing of R-fasoracetam monohydrate Form II.
Figure 11:
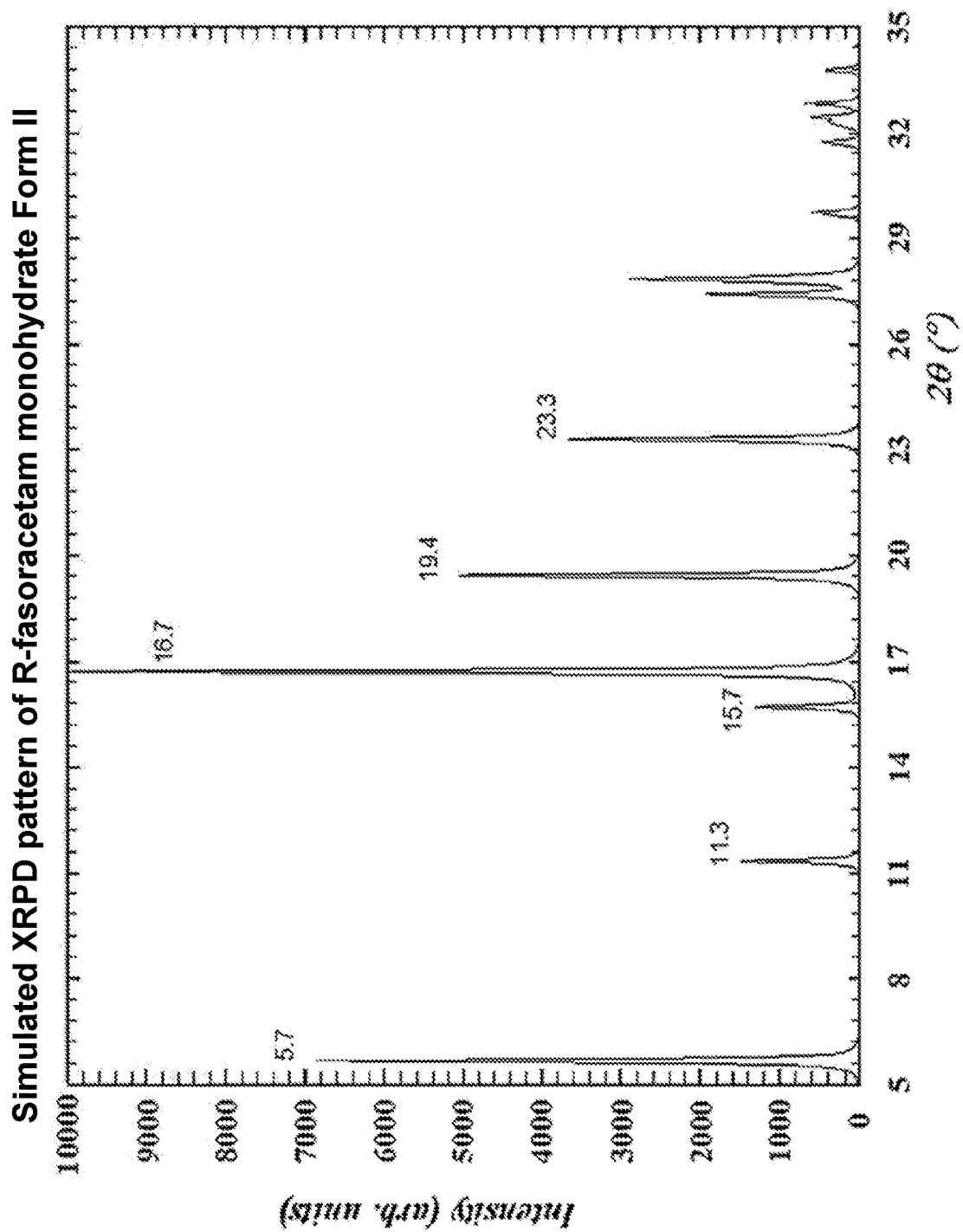
FIG. 11 is a simulated XRPD pattern of R-fasoracetam monohydrate Form II.

R-fasoracetam monohydrate Form I from Jinan Haohua Industry Co., Ltd. was dissolved in methanol. The solution was then left to slowly evaporate at room temperature to yield a crystalline material. A simulated x-ray powder pattern was prepared from the single crystal data solution and compared with the experimentally obtained powder pattern of Example 1 (FIG. 4) and is shown in FIG. 9. An ORTEP drawing is found at FIG. 10 and Table 1 is a list of single crystal data parameters. FIG. 11 is the simulated XRPD pattern.

TABLE 1

Crystal data and structure refinement for R-fasoracetam monohydrate Form II

| Parameter | Results |
|---|---|
| Empirical formula | $C_{10} H_{18} N_2 O_3$ |
| Formula weight | 214.26 |
| Temperature | 150(2) K |
| Wavelength | 0.71073 Å |
| Crystal system | Monoclinic |
| Space group | C2 |

TABLE 1-continued

Crystal data and structure refinement for R-fasoracetam monohydrate Form II

| Parameter | Results | |
|---|---|---|
| Unit cell dimensions | a = 11.2982(6) Å | α = 90°. |
| | b = 6.5055(4) Å | β = 90.291(5)°. |
| | c = 15.6050(10) Å | γ = 90°. |
| Volume | 1146.97(12) Å3 | |
| Z | 4 | |
| Density (calculated) | 1.241 Mg/m3 | |
| Absorption coefficient | 0.092 mm−1 | |
| F(000) | 464 | |
| Crystal size | 0.300 × 0.050 × 0.030 mm3 | |
| Theta range for data collection | 3.607 to 25.179°. | |
| Index ranges | −13 <= h <= 13, −7 <= k <= 7, −18 <= l <= 18 | |
| Reflections collected | 4481 | |
| Independent reflections | 2027 [R(int) = 0.0324] | |
| Completeness to theta = 25.179° | 99.5% | |
| Absorption correction | Semi-empirical from equivalents | |
| Max. and min. transmission | 1.00000 and 0.94436 | |
| Refinement method | Full-matrix least-squares on F2 | |
| Data/restraints/parameters | 2027/1/139 | |
| Goodness-of-fit on F2 | 1.080 | |
| Final R indices [I > 2sigma(I)] | R1 = 0.0412, wR2 = 0.0916 | |
| R indices (all data) | R1 = 0.0539, wR2 = 0.0966 | |
| Absolute structure parameter | 0.2(8) | |
| Extinction coefficient | n/a | |
| Largest diff. peak and hole | 0.176 and −0.146 e · Å−3 | |

Example 4

Single Crystal Fasoracetam Anhydrate

Figure 14:
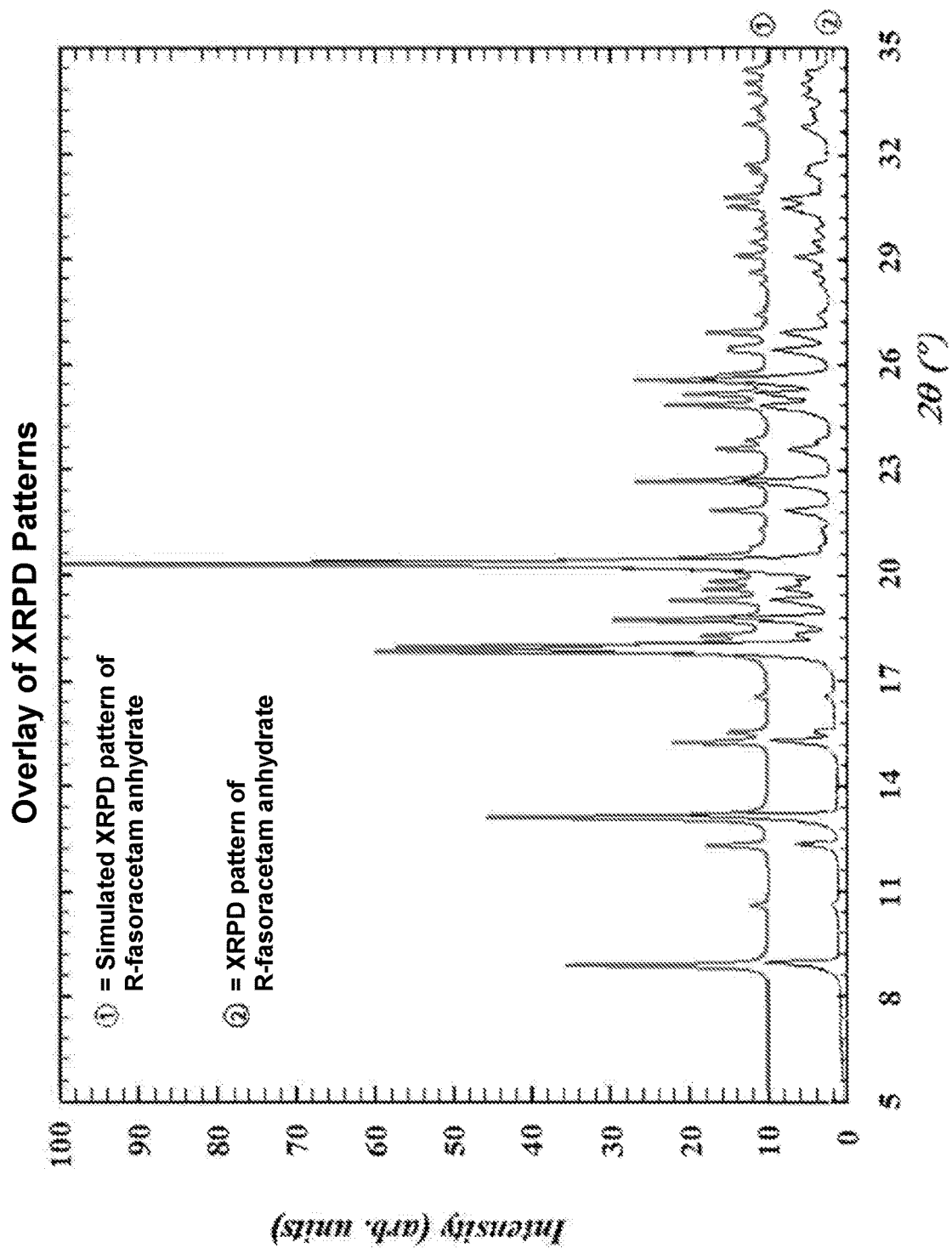
FIG. 14 is an overlay of XRPD patterns: (1) Simulated XRPD pattern of R-fasoracetam anhydrate; (2) XRPD pattern of R-fasoracetam anhydrate.

R-fasoracetam monohydrate Form I from Jinan Haohua Industry Co., Ltd. was placed under vacuum at 60° C. and melting was observed. After one week, the temperature was lowered maintaining vacuum conditions. Crystalline material appeared and was found to be R-fasoracetam anhydrate. An ORTEP drawing is found at FIG. 12, and Table 2 is a list of single crystal data parameters. FIG. 13 is the simulated XRPD pattern and FIG. 14 is an overlay of the simulated pattern and that of R-fasoracetam anhydrate.

TABLE 2

Crystal data and structure refinement for fasoracetam anhydrate

| Parameter | Results | |
|---|---|---|
| Empirical formula | $C_{10} H_{16} N_2 O_2$ | |
| Formula weight | 196.25 | |
| Temperature | 297(2) K | |
| Wavelength | 0.71073 Å | |
| Crystal system | Orthorhombic | |
| Space group | $P2_1 2_1 2_1$ | |
| Unit cell dimensions | a = 9.2095(5) Å | α = 90°. |
| | b = 11.5104(8) Å | β = 90°. |
| | c = 19.7276(13) Å | γ = 90°. |
| Volume | 2091.2(2) Å3 | |
| Z | 8 | |
| Density (calculated) | 1.247 Mg/m3 | |
| Absorption coefficient | 0.088 mm−1 | |
| F(000) | 848 | |
| Crystal size | 0.5 × 0.4 × 0.4 mm3 | |
| Theta range for data collection | 3.015 to 25.206°. | |

TABLE 2-continued

Crystal data and structure refinement for fasoracetam anhydrate

| Parameter | Results |
|---|---|
| Index ranges | -10 <= h <= 10, -13 <= k <= 12, -23 <= l <= 23 |
| Reflections collected | 8790 |
| Independent reflections | 3731 [R(int) = 0.0335] |
| Completeness to theta = 25.206° | 99.2% |
| Absorption correction | Semi-empirical from equivalents |
| Max. and min. transmission | 1.00000 and 0.42311 |
| Refinement method | Full-matrix least-squares on F2 |
| Data/restraints/parameters | 3731/12/308 |
| Goodness-of-fit on F2 | 1.016 |
| Final R indices [I > 2sigma(I)] | R1 = 0.0441, wR2 = 0.1139 |
| R indices (all data) | R1 = 0.0539, wR2 = 0.1218 |
| Absolute structure parameter | -0.6(7) |
| Extinction coefficient | n/a |
| Largest diff. peak and hole | 0.126 and -0.134 e · Å-3 |

Example 5

Single Crystal of R-Fasoracetam Monohydrate Form I

Figure 15:
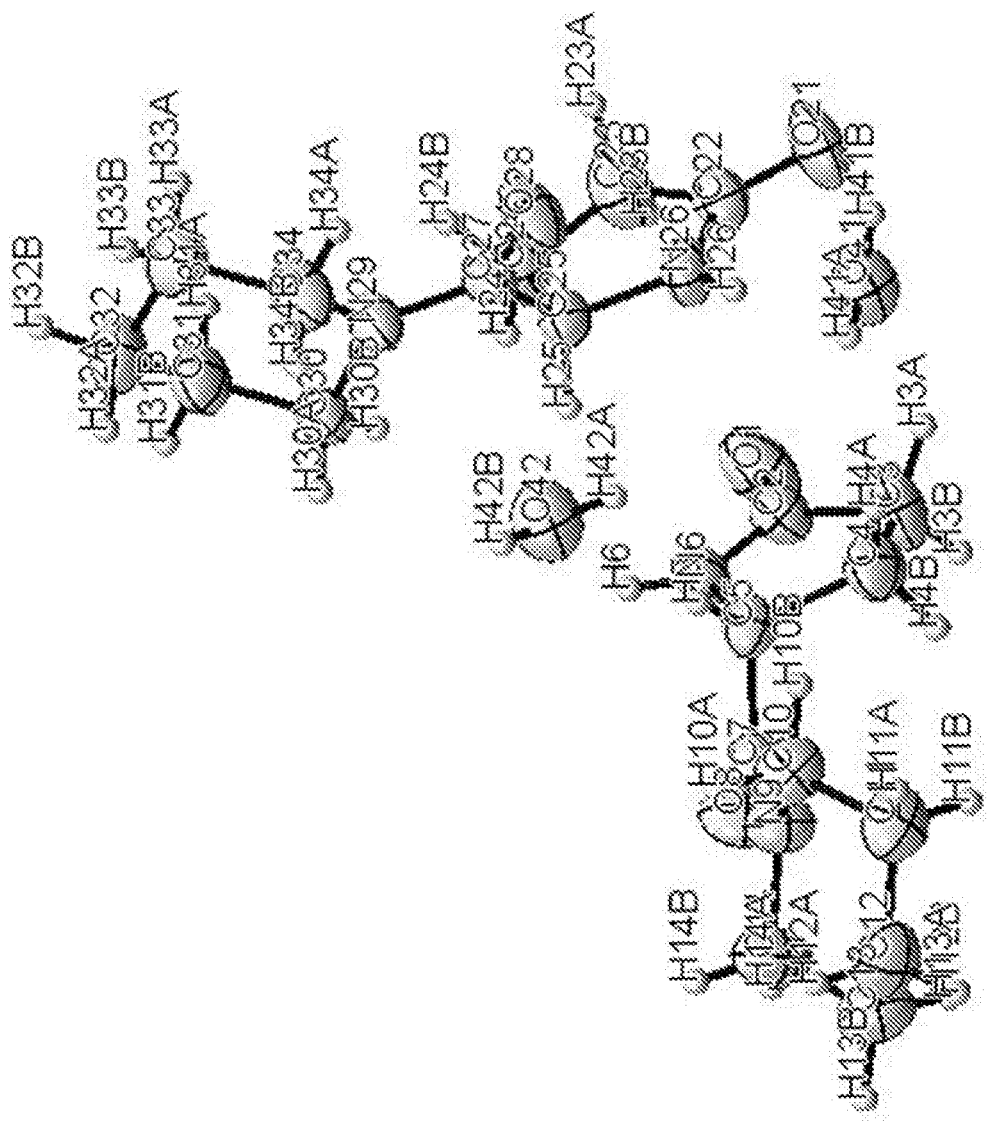
FIG. 15 is an ORTEP drawing of R-fasoracetam monohydrate Form I.
Figure 16:
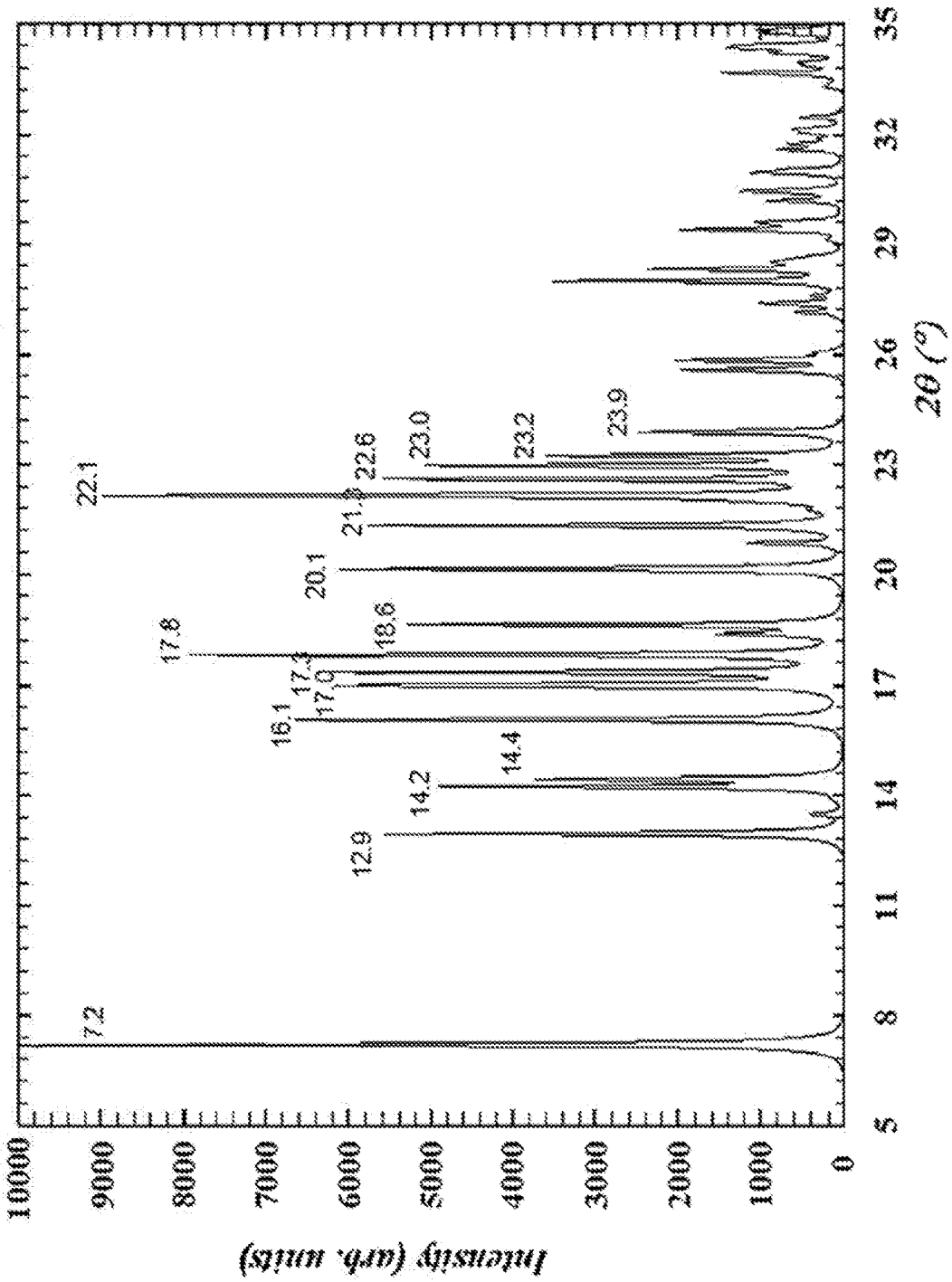
FIG. 16 is a simulated XRPD pattern of R-fasoracetam monohydrate Form I.
Figure 17:
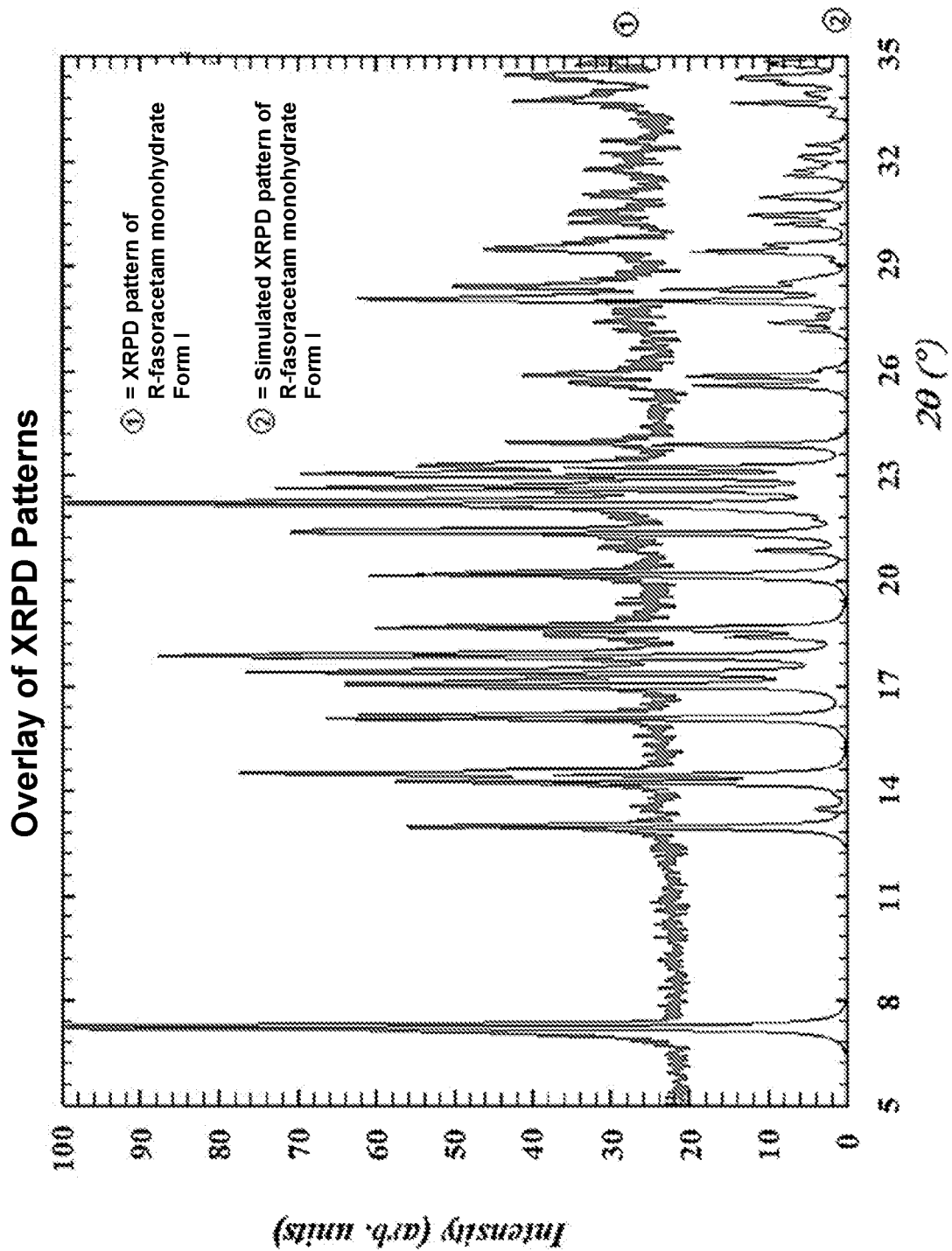
FIG. 17 is an overlay of XRPD patterns: (1) XRPD pattern of R-fasoracetam monohydrate Form I; (2) Simulated XRPD pattern of R-fasoracetam monohydrate Form I.

R-fasoracetam monohydrate Form I from Jinan Haohua Industry Co., Ltd. is dissolved in water. The solution was then left to slowly evaporate at room temperature to yield a crystalline material which was analyzed and found to be R-fasoracetam monohydrate Form I. An ORTEP drawing is found at FIG. 15, and Table 3 is a list of single crystal data parameters. FIG. 16 is a simulated XRPD pattern and FIG. 17 is an overlay of the simulated pattern and that of R-fasoracetam monohydrate Form I indicating a match.

TABLE 3

Crystal data and structure refinement for R-fasoracetam monohydrate Form I

| Parameter | Results |
|---|---|
| Empirical formula | C10 H18 N2 O3 |
| Formula weight | 214.26 |
| Temperature | 297(2) K |
| Wavelength | 0.71073 Å |
| Crystal system | Triclinic |
| Space group | P1 |
| Unit cell dimensions | a = 6.6093(7) Å   α = 99.691(10)°. |
|  | b = 7.0801(7) Å   β = 100.272(10)°. |
|  | c = 12.7221(18) Å   γ = 99.363(9)°. |
| Volume | 565.91(12) Å3 |
| Z | 2 |
| Density (calculated) | 1.257 Mg/m3 |
| Absorption coefficient | 0.093 mm-1 |
| F(000) | 232 |
| Crystal size | 0.21 × 0.11 × 0.05 mm3 |
| Theta range for data collection | 3.102 to 25.525°. |
| Index ranges | -7 <= h <= 7, -8 <= k <= 8, -15 <= l <= 15 |
| Reflections collected | 7583 |
| Independent reflections | 4076 [R(int) = 0.0514] |
| Completeness to theta = 25.242° | 99.3% |
| Absorption correction | Semi-empirical from equivalents |
| Max. and min. transmission | 1.00000 and 0.75526 |
| Refinement method | Full-matrix least-squares on F2 |
| Data/restraints/parameters | 4076/3/277 |
| Goodness-of-fit on F2 | 1.054 |

TABLE 3-continued

Crystal data and structure refinement for R-fasoracetam monohydrate Form I

| Parameter | Results |
|---|---|
| Final R indices [I > 2sigma(I)] | R1 = 0.0455, wR2 = 0.1137 |
| R indices (all data) | R1 = 0.0567, wR2 = 0.1217 |
| Absolute structure parameter | -1.4(10) |
| Extinction coefficient | n/a |
| Largest diff. peak and hole | 0.131 and -0.121 e · Å-3 |

Example 6

R-Fasoracetam Screen

The three solid forms: Form I, II, and the anhydrate were found in a screen of R-fasoracetam. Initially, a first screen was performed based on the solvent evaporation principle. The purchased compound was dissolved in the solvents investigated and the solution was left to evaporate completely. Once the solution was evaporated completely, the powders obtained from the solvent screen were directly analyzed using XRPD and it was confirmed that they were Form I and Form II as described herein. The results obtained are shown in Table 4.

TABLE 4

Solvent-based Solid Form Screen for Fasoracetam

| Solvent | Crystal Form (XPRD) |
|---|---|
| Water | Hydrate I |
| Acetonitrile | Hydrate II |
| Methanol | Hydrate II |
| Ethyl acetate | Hydrate I |
| Acetone | Hydrate I |
| Dichloromethane | Hydrate II |
| Tetrahydrofuran | Hydrate I |
| Chloroform | Hydrate II |
| Toluene | Hydrate II |

Solvent evaporation did not lead to the formation of R-fasoracetam anhydrate. The hydrate form obtained from each solvent (Form I or Form II) appears to be random, as no correlation among evaporation rate, hygroscopicity, and polarity were found. Crystals obtained by water and methanol evaporation were found suitable for SC-XRD analysis, which showed a 1:1 stoichiometric hydrate form in both cases (Form I and Form II).

Figure 18:
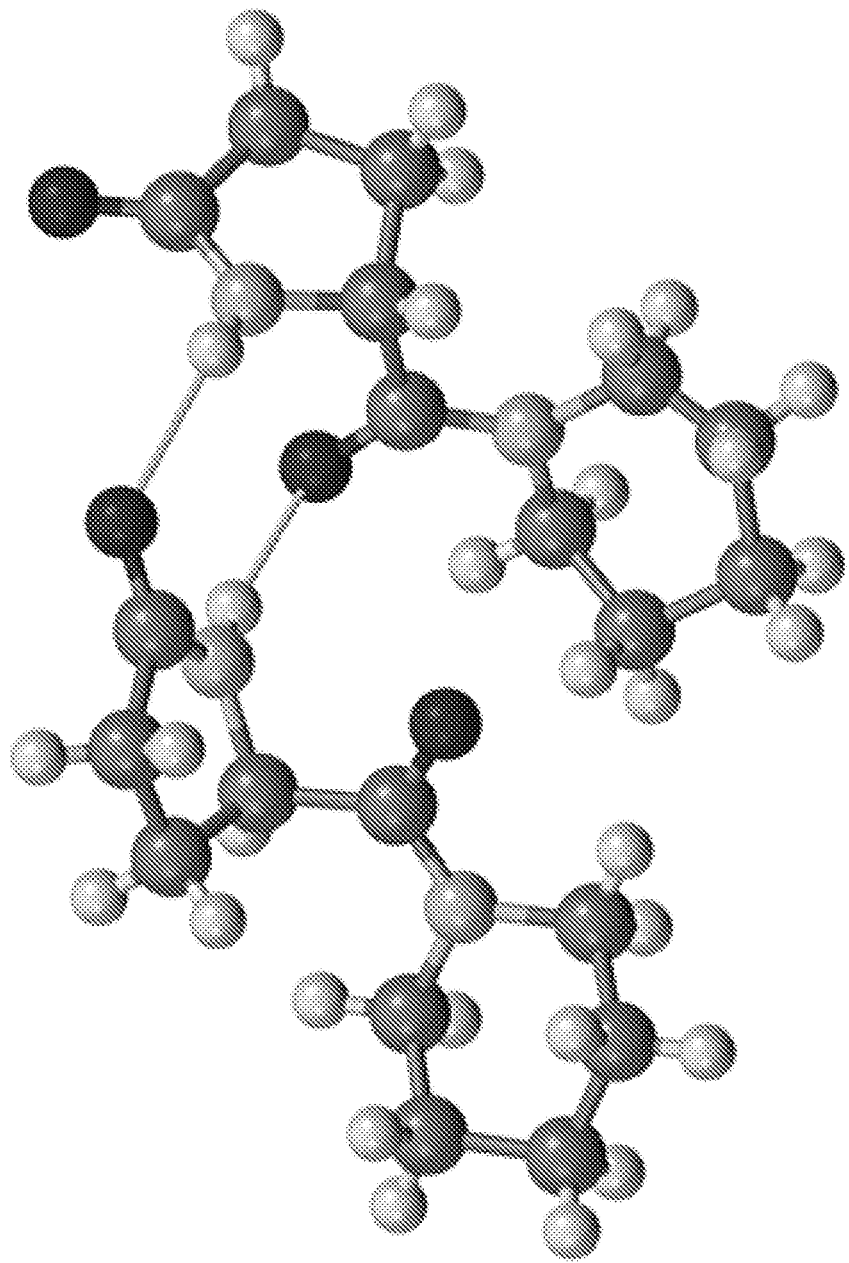
FIG. 18 is a hydrogen bonding pattern of the anhydrate

FIG. 18 shows the hydrogen bonding pattern for the anhydrate phase. This bonding network corresponds to an $R^2_2(9)$ synthon (Etter's graph set notation), composed of a N—H group of the pyrrolidone ring of the first molecule forming a hydrogen bond with the pyrrolidone carbonyl of a second molecule. A second hydrogen bond links the bridging carbonyl of the first molecule to the N—H group in the pyrrolidone ring of the second molecule. This hydrogen bonding pattern is the only pattern present in the crystal structure.

The hydrate form I of fasoracetam (FIG. 19) is a stoichiometric hydrate with one water molecule per fasoracetam molecule. The high number of hydrogen donors and acceptors present create a complex hydrogen bonding network. The water molecules serve as bridge between fasoracetam molecules with both hydrogens forming a bond with a carbonyl group of 2 different pyrrolidone rings. A second hydrogen bond from the N—H group on the first pyrrolidone ring to the carbonyl on the second leads to a closed-ring $R^2_2(8)$ pattern, which can be seen in the center-bottom of FIG. 19.

Figure 19:
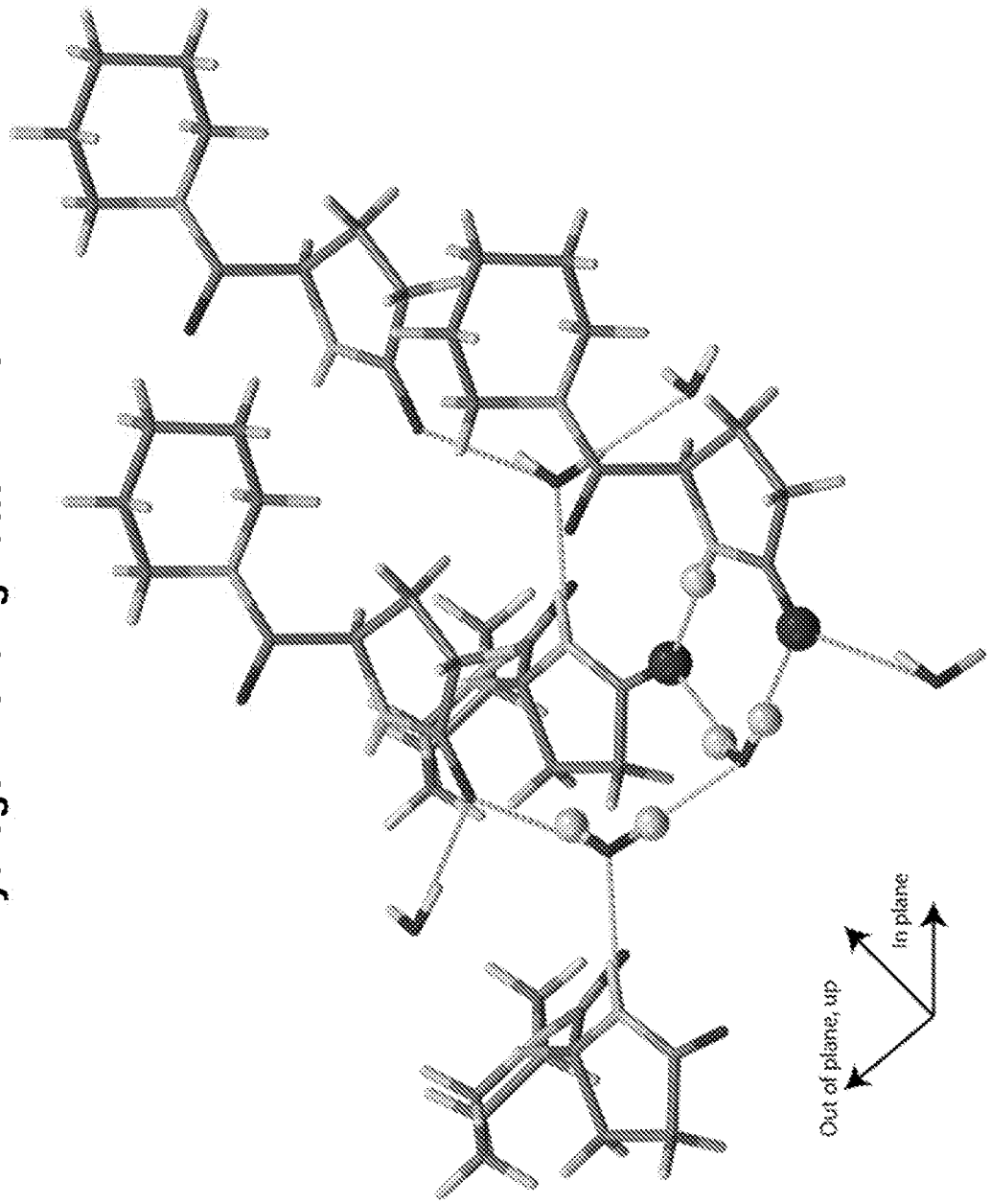
FIG. 19 is a hydrogen bonding pattern of Form I.

As shown in FIG. 19, it is important to note that the water molecule functioning as a double donor lies flat in the plane with both pyrrolidone moieties of the fasoracetam molecules. This interaction, as described above, creates a ring-like arrangement of water and fasoracetam molecules all within the same plane as emphasized by the ball and stick representation. Interestingly, the water molecule serving as a double hydrogen donor in the ring arrangement also acts as an acceptor for a second water molecule, having a proton lying perpendicular to the aforementioned plane. This hydrogen bond connects the different ring-like arrangements in a step-like pattern from an extended point of view. The hydrogen bonds described here can be described as $D^3_3(6)$. Therefore, the water molecules can also be seen as molecules that connect different planes.

Figure 20:
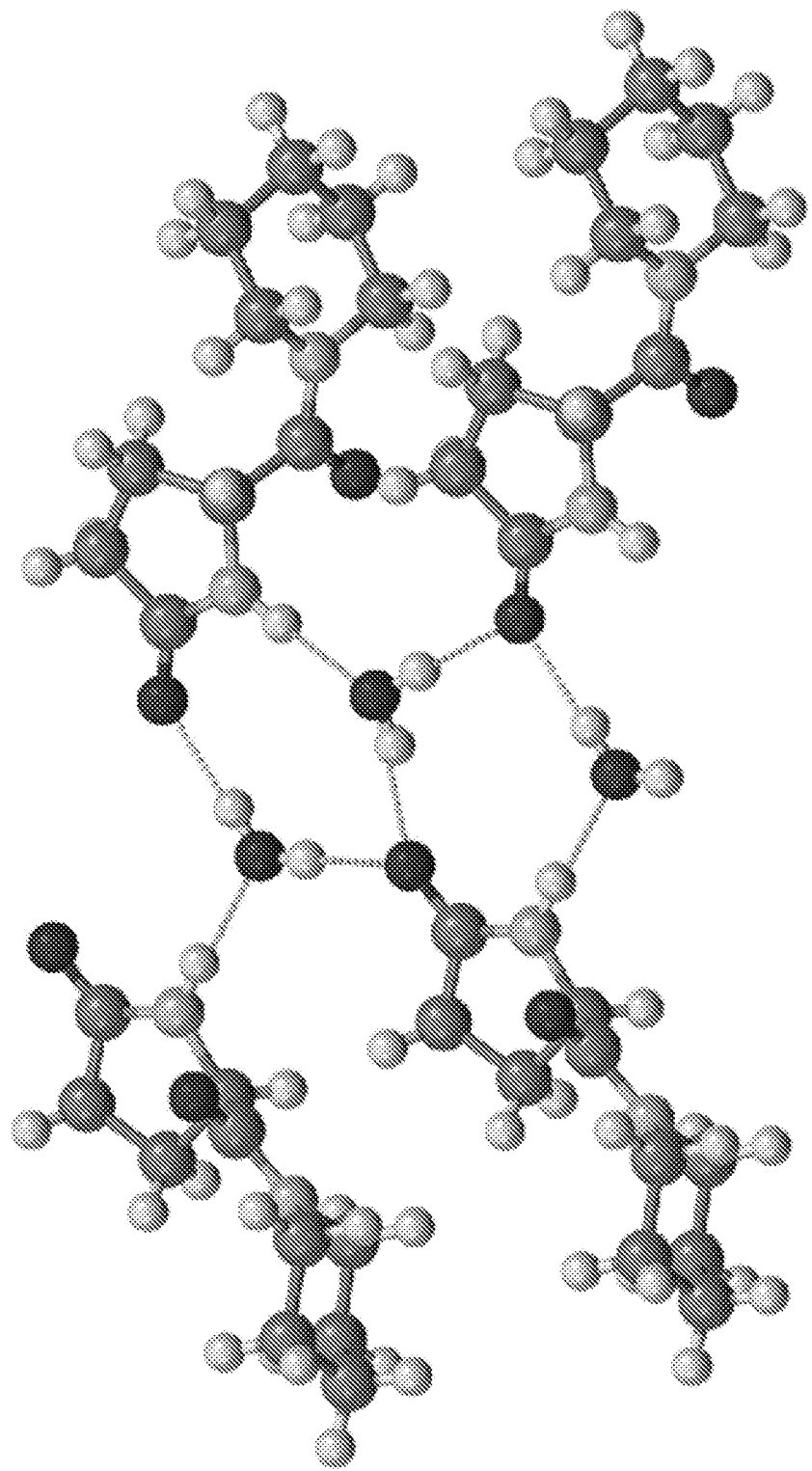
FIG. 20 is a hydrogen bonding pattern of Form II.

In FIG. 20, the hydrogen bonding pattern of the hydrate form II is shown. The main difference between this and the previous hydrate form is the location of the water molecules. All hydrogen bonds lie within the same plane, forming a sheet. Contrary to hydrate form I, there are no hydrogen bonds out of the plane, linking the sheets together. Additionally, where in Form I fasoracetam molecules directly form hydrogen bonds with each other, this is not observed in hydrate Form II and all hydrogen bonds go via water molecules. Sheets are therefore held together by interactions other than hydrogen bonding ones, which will likely explain why this hydrate form is less stable, as shown later on. Each water molecule serves as a double hydrogen donor, forming hydrogen bonds with the pyrrolidone carbonyl groups of 2 distinct fasoracetam molecules. Simultaneously, the same water molecule also acts as an acceptor, forming a hydrogen bond with the pyrrolidone N—H group of a third fasoracetam molecule. These interactions connect the whole sheet together and can be described as $R^3_4(10)$. Crystal structure data tables are further presented below in Table 5 (some data are already present in Tables 1, 2, and 3).

TABLE 5

Crystal Structure Data of All Fasoracetam Forms

| Parameter | Fasoracetam Hydrate I | Fasoracetam Hydrate II | Fasoracetam Anhydrate |
|---|---|---|---|
| Cambridge Crystallographic Data Center number | 1489556 | 1489557 | 1489558 |
| Chemical formula | C10H16N2O2•H2O | C10H16N2O2•H2O | C10H16N2O2 |
| Mr | 214.26 | 214.26 | 196.25 |
| Crystal system, space group | Triclinic, P1 | Monoclinic, C2 | Orthorhombic, P212121 |
| Temperature (K) | 297 | 150 | 297 |
| a, b, c (Å) | 6.6093 (7), 7.0801 (7), 12.7221 (18) | 11.2982 (6), 6.5055 (4), 15.6050 (10) | 9.2095 (5), 11.5104 (8), 19.7276 (13) |
| α, β, γ (°) | 99.691 (10), 100.272 (10), 99.363 (9) | 90, 90.291 (5), 90 | 90, 90, 90 |
| V (Å3) | 565.91 (12) | 1146.96 | 2091.2 (2) |
| Z | 2 | 4 | 8 |
| Radiation type | MoKα | MoKα | MoKα |
| μ (/mm) | 0.09 | 0.09 | 0.09 |
| Crystal size (mm) | 0.21 × 0.11 × 0.05 | 0.30 × 0.05 × 0.03 | 0.5 × 0.4 × 0.4 |
| Tmin, Tmax | 0.755, 1.000 | 0.944, 1.000 | 0.423, 1.000 |
| No. of measured, independent, observed [I > 2σ(I)] reflections | 7583, 4076, 3401 | 4481, 2027, 1737 | 8790, 3731, 3160 |
| Rint | 0.051 | 0.032 | 0.034 |
| θmax | 25.525 | 25.179 | 25.206 |
| R [F2 > 2σ(F2)], wR(F2), S | 0.046, 0.122, 1.05 | 0.041, 0.097, 1.06 | 0.044, 0.122, 1.02 |
| No. of parameters | 277 | 143 | 308 |
| No. of restraints | 3 | 1 | 12 |
| Δρmax, Δρmin (e/Å3) | 0.13, −0.12 | 0.18, −0.14 | 0.13, −0.13 |

As shown by this table, when the z value for hydrate II is adjusted to one formula unit its volume becomes 286.74 Å3. This is slightly bigger than the volume taken by hydrate form I, 282.96 Å3. It seems that the reorientation of one of the water molecules for hydrate I results in a slightly more compressed structure as a whole, which could yield stronger (shorter) hydrogen bonds or the formation of new hydrogen bonds due to the molecules' closer proximity. However, because the data have been collected at different temperatures (150 K for Form II and 297 K for Form I), the difference is likely negligible. When both hydrate forms are compared for the number and composition of hydrogen bonds, the increased stability for Form I becomes apparent. Form II has a total of 5 unique hydrogen bonds, all of them with water molecules. The more stable form, Form I, has 10 unique hydrogen bonds and these are made up of hydrogen bonds with water molecules like in Form II, but hydrogen bonds directly between fasoracetam molecules are also present. The increased amount of unique hydrogen bonds together with different hydrogen bond types is the likely reason for the higher stability of Form I.

Figure 21:
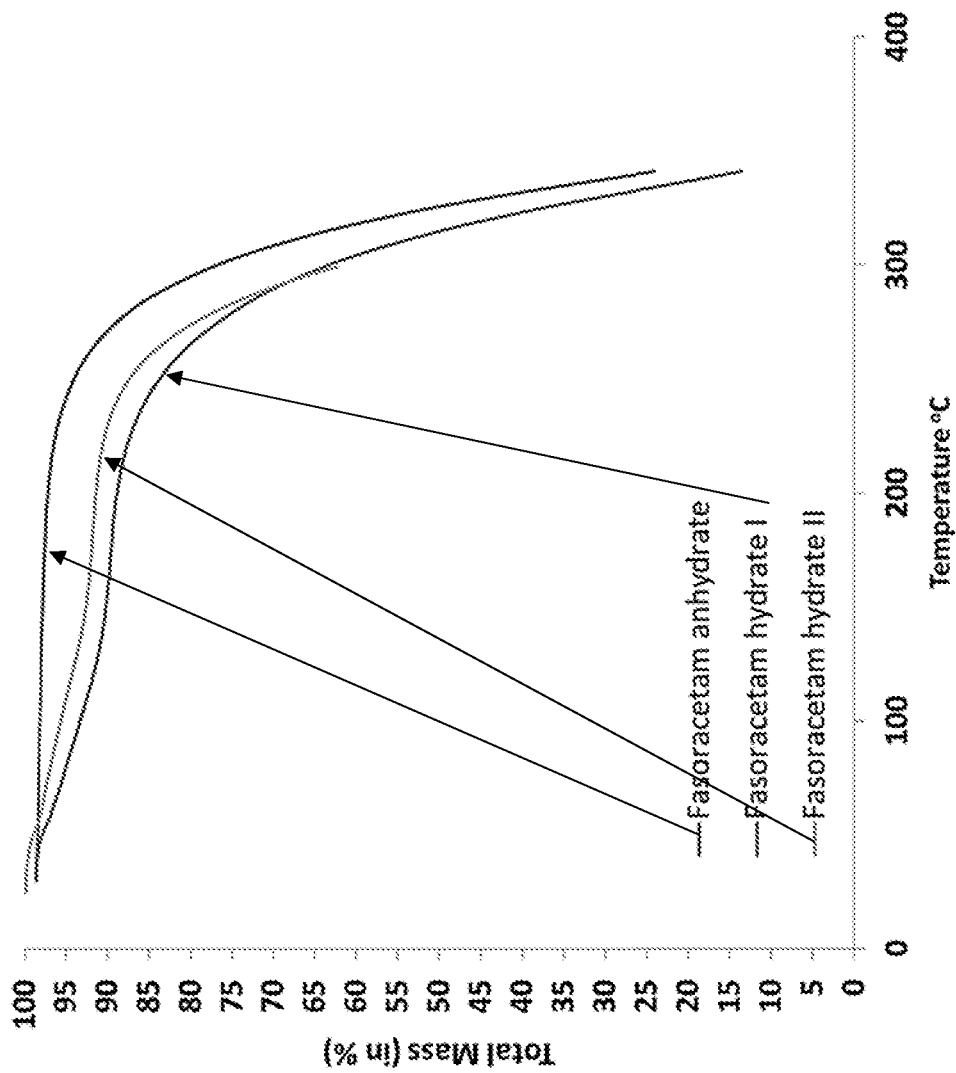
FIG. 21 is an overlay of TGA measurements.

A thermal analysis of all forms was performed in order to characterize the fasoracetam forms and to identify the stability of different forms. TGA measurements (FIG. 21) clearly mark the difference between the hydrated and anhydrated form. The anhydrate clearly shows no particular weight loss up until degradation, which occurs at around 260° C. The Form I (blue line), on the other hand, shows a first onset of weight loss at 41° C. The weight loss continues up to 185° C. When the temperature is increased further, degradation occurs, starting around 260° C. The initial loss corresponds to 1.1 equivalent of water, as expected for a 1:1 stoichiometric hydrate. The slight deviation from the ideal stoichiometric ratio can be attributed to the crystallization conditions (the bulk material was obtained from an aqueous solution and the water remaining on the crystal surface or trapped between crystals is likely to cause the deviation observed). The Form II also shows a first onset of weight loss at 41° C. and continues up to 183° C. Analogous to Form I, degradation occurs which starts around 268° C. The observed water loss here is 0.9 equivalent, which is expected for a stoichiometric hydrate.

Figure 22:
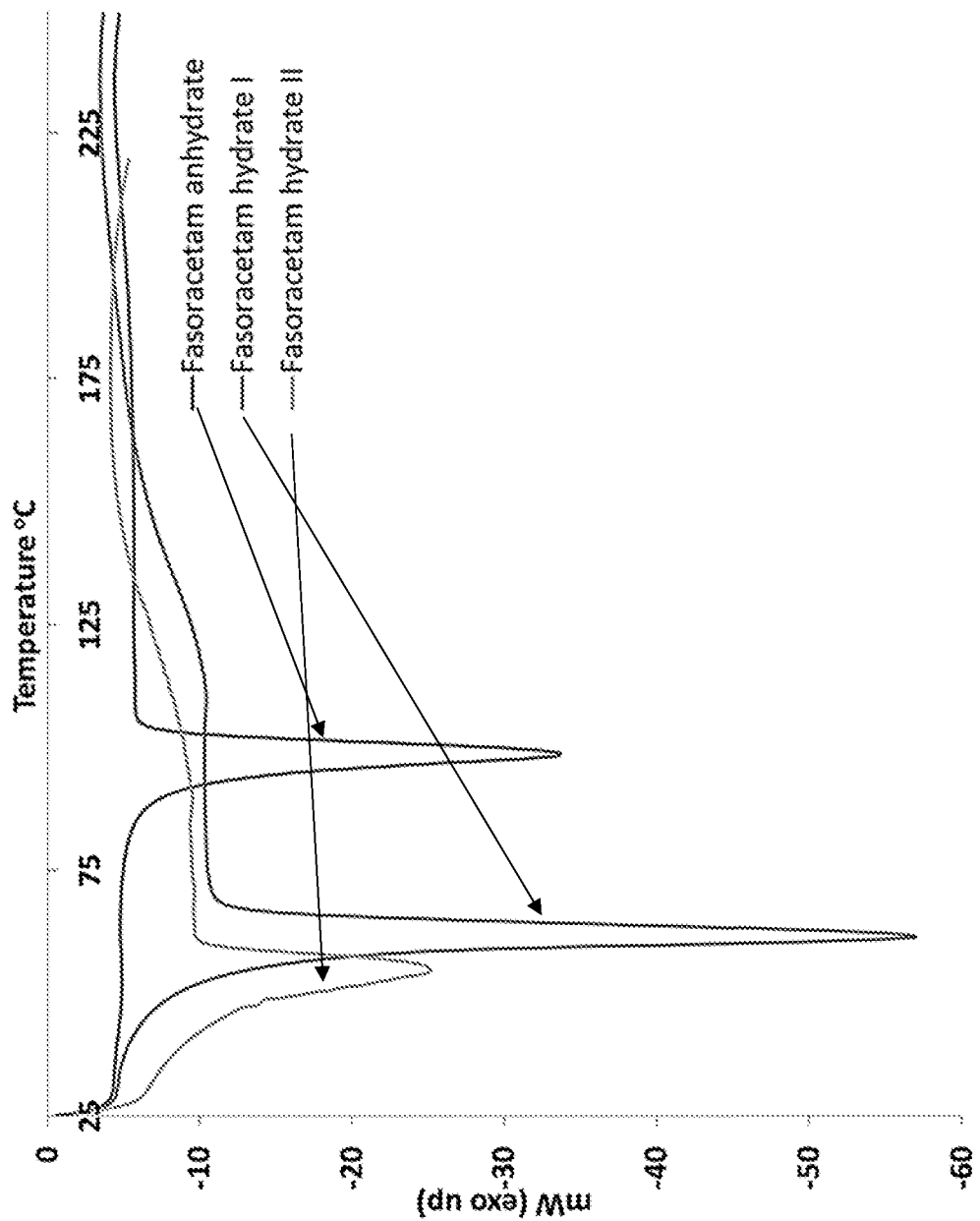
FIG. 22 is an overlay of DSC measurements.

The DSC measurements (FIG. 22) show clear single melting events for all forms, as depicted by the sharp endothermic peaks. In the case of fasoracetam Form II, the onset of the melting point was determined at 47.8° C. For fasoracetam Form I, the onset of the melting point was determined at 57.2° C. This explains that the expected loss in mass starting at 41° C. (TGA measurement) is likely due to surface water. The continuation of mass loss occurs upon melting of the sample. The continued energy input (extended shoulder following the melting peak) after melting suggests that water is evaporating. This finding is supported by the other hydrate, Form II, which exhibits the same behavior. The evaporation continues up until around 185° C., which is in agreement with the data obtained from the TGA. The melting points of Form I and Form II occur prior to the water loss. This indicates that water is lost after melting and one is not dealing with dehydration of the hydrate to yield an amorphous or other anhydrous crystalline form. This is furthermore confirmed visually when the sample is heated to 60° C. As expected, the anhydrate form shows a single melting point, with an onset at 92.6° C. The relatively small difference in melting points between the 2 hydrated forms could suggest that a solid-solid phase transformation can occur. Taking the structural data into account, it would most likely consist of a transformation from a two-dimensional sheet-like hydrogen bonding network (Form II) to a three-dimensional connected sheets hydrogen bonding network. The large difference in melting points between the hydrates and the anhydrate form suggests that conversion of the hydrates into the anhydrate is unlikely at ambient conditions. Investigation of the anhydrate shows that conversion to the stable hydrate occurs at ambient conditions over a 1-week period (the conversion was tracked on a daily basis via XRPD).

Using Burger's Heat of Fusion rule for both hydrated forms (Table 6), they should be monotropically related. Because both hydrates were obtained from different solvents (water and methanol for Forms I and II, respectively), a slurrying experiment where both vials were seeded with the opposite hydrate was performed and left under these conditions for 1 week. After analyzing both vials with XRPD, it turned out that both contained Form I suggesting complete solution mediated polymorphic transition from Form II to Form I. Therefore, we can conclude that Form II is the less stable hydrate.

TABLE 6

Enthalpies of Fusion for Fasoracetam Forms
Enthalpy of Fusion ($\Delta$Hfus, J/g)

| Fasoracetam hydrate I | Fasoracetam hydrate II | Fasoracetam anhydrate |
| --- | --- | --- |
| −120.9 J/g | −79.0 J/g | −76.7 J/g |

Figure 23:
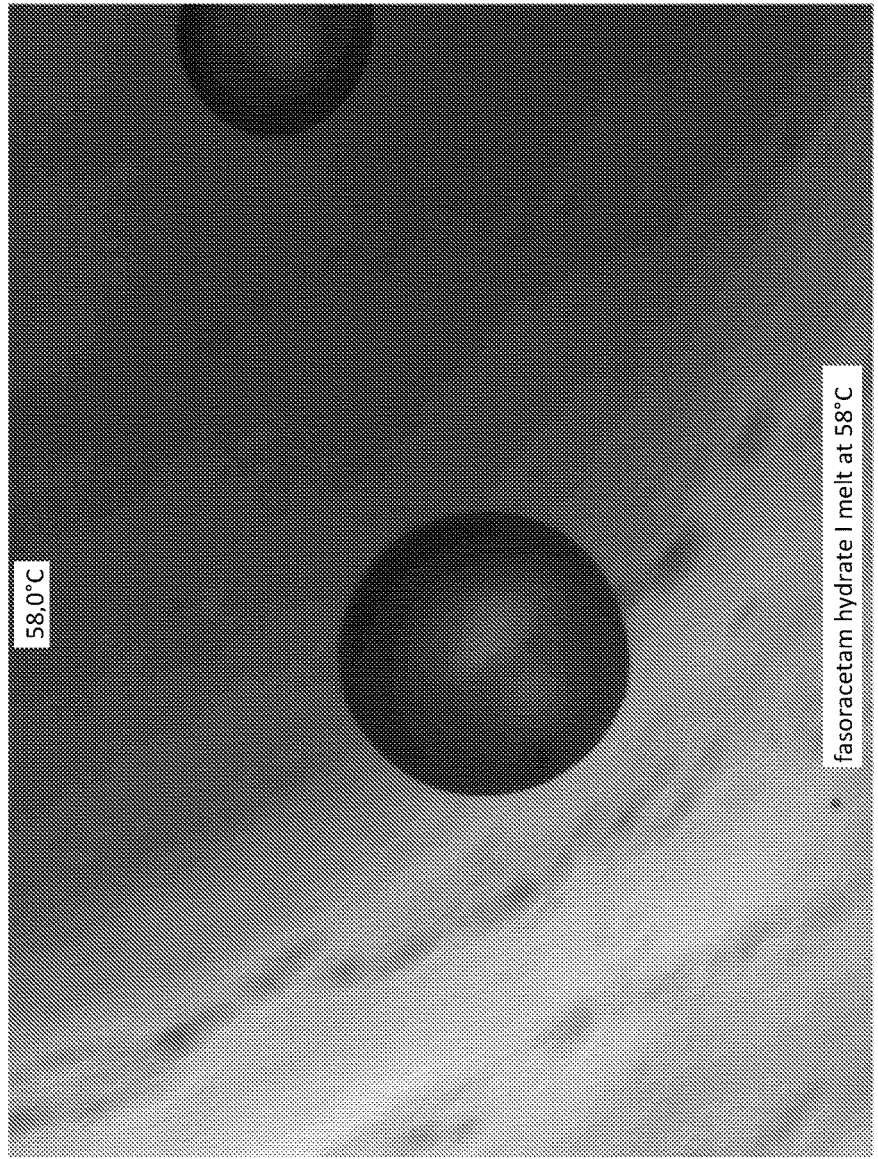
FIG. 23 is a hot stage microscope picture of fasoracetam hydrate Form I.
Figure 24:
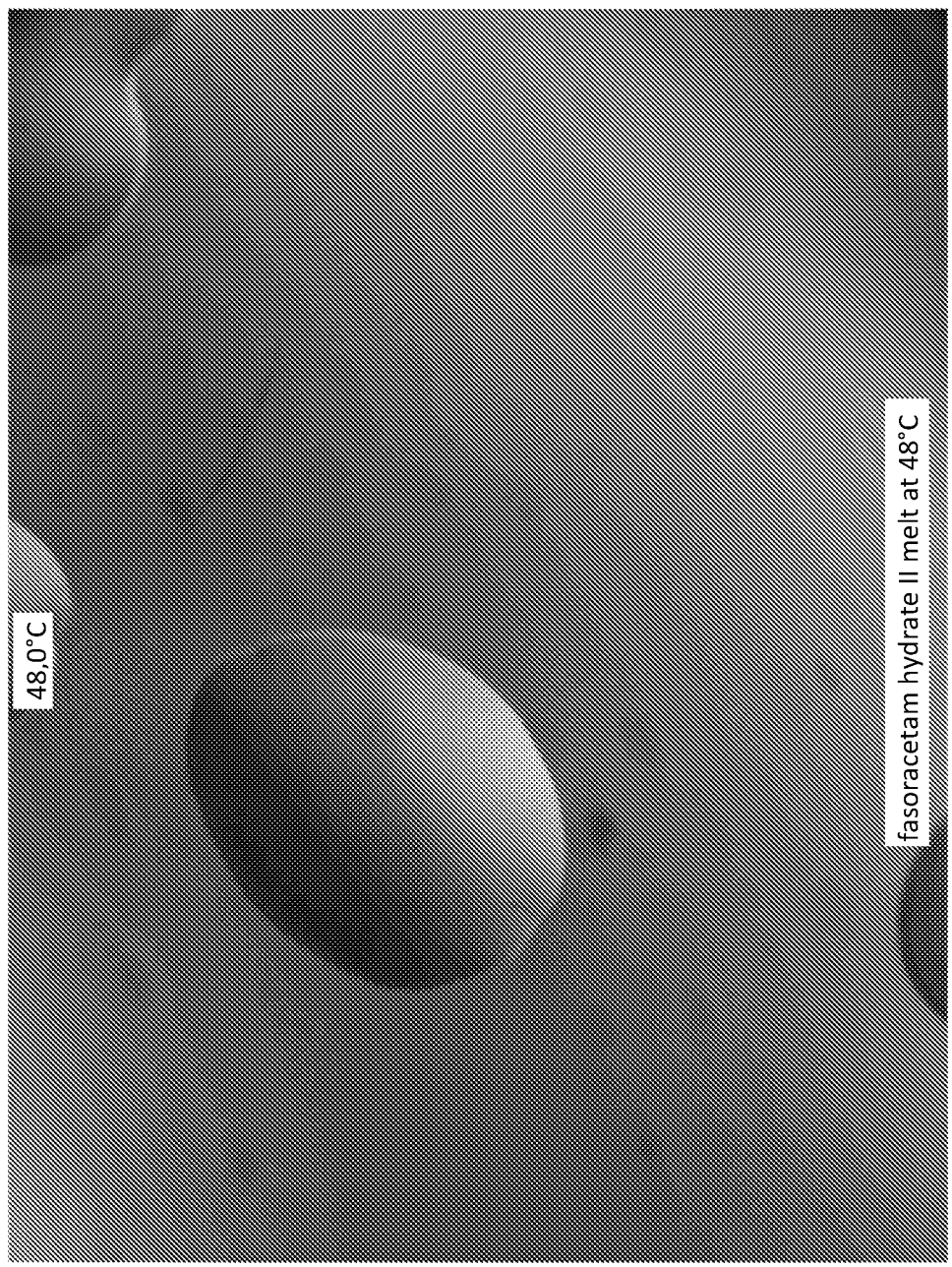
FIG. 24 is a hot stage microscope picture of fasoracetam hydrate Form II.

For organic molecules that contain solvent in their crystalline form, dehydration or desolvation can occur before or after melting. In the specific case of fasoracetam, melting occurs before dehydration. To verify this, both hydrated forms were placed under a hot stage microscope and pictures proving the melt at the determined melting points have been taken. The pictures for Form I and II can be found in FIGS. 23 and 24, respectively. The sole purpose of these images is to confirm that melting occurs (as shown via DSC) and no other phase transformations take place.

What is claimed is:

1. A solid form of R-fasoracetam monohydrate, wherein the solid form has an x-ray diffraction pattern comprising one or more peaks chosen from peaks at 5.6 ±0.2°2θ, 11.3±0.2°2θ, and 19.4±0.2°2θ.

2. The solid form of claim 1, wherein the solid form has an onset melting temperature of 48.80±3° C.

3. The solid form of claim 1, wherein the x-ray powder diffraction pattern further comprises one or more peaks at 16.7±0.2°2θ, 23.3±0.2°2θ, and 27.6±0.2°θ.

* * * * *